United States Patent [19]

Feng et al.

[11] Patent Number: 5,731,343
[45] Date of Patent: Mar. 24, 1998

[54] METHOD OF USE OF RADICICOL FOR TREATMENT OF IMMUNOPATHOLOGICAL DISORDERS

[75] Inventors: Lili Feng, San Diego, Calif.; Daniel Hwang, Baton Rouge, La.

[73] Assignees: The Scripps Research Institute, La Jolla, Calif.; Board of Supervisors of Louisiana State University and Agricultural and Mechanical College, Baton Rouge, La.

[21] Appl. No.: 394,148

[22] Filed: Feb. 24, 1995

[51] Int. Cl.$^6$ ................................. A61K 31/335
[52] U.S. Cl. ................................. 514/450
[58] Field of Search ................................. 514/450

[56] References Cited

U.S. PATENT DOCUMENTS

| | | | |
|---|---|---|---|
| 4,166,764 | 9/1979 | Calton et al. | 435/119 |
| 4,228,079 | 10/1980 | Calton | 549/268 |
| 4,707,492 | 11/1987 | Myers-Keith et al. | 514/450 |

FOREIGN PATENT DOCUMENTS

| | | |
|---|---|---|
| 0460950 | 12/1991 | European Pat. Off. . |
| 0606044 | 7/1994 | European Pat. Off. . |
| 9118905 | 12/1991 | WIPO . |

OTHER PUBLICATIONS

Kown et al, *Chemical Abstracts*, vol. 118, No. 11, abstract No. 93893m, 1993, p. 28.

*Primary Examiner*—Marianne M. Cintins
*Assistant Examiner*—William R. A. Jarvis
*Attorney, Agent, or Firm*—Fish & Richardson, P.C.

[57] ABSTRACT

The present invention provides a method of treating an immunopathological disorder having an etiology associated with production of a proinflammatory agent, by administering a compound of the formula:

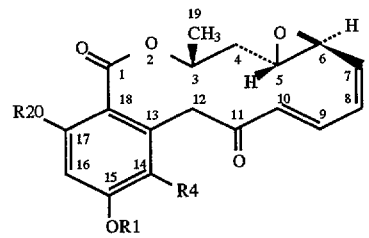

where R1 and R2 are independently H or —COR3; R3 is H, 1–50C alkyl, 1–20C alkoxy, 2–30C alkenyl, 2–30C alkenyloxy, 2–10 alkynyl, 6–14C aryl or aryloxy, a 5–6 membered heterocycle (containing 1–3 N, O and/or S heteroatoms and optionally fused to an aryl group), 3–8C cycloalkyl (optionally fused to aryl) or 5–8C cycloalkenyl; and R4 is a halogen. Examples of such proinflammatory agents include interleukin-1 (IL-1), interleukin-6 (IL-6), interferon-γ (IFN-γ), tumor necrosis factor-α (TNF-α), granulocyte macrophage-colony stimulating factor (GM-CSF), the growth related gene KC, cyclooxygenase-1 (COX-1), cyclooxygenase-2 (COX-2), macrophage chemotactic protein (MCP), inducible nitric oxide synthetase (iNOS), macrophage inflammatory protein (MIP), tissue factor (TF), phosphotyrosine phosphatase (PTPase), and endotoxin.

8 Claims, 24 Drawing Sheets

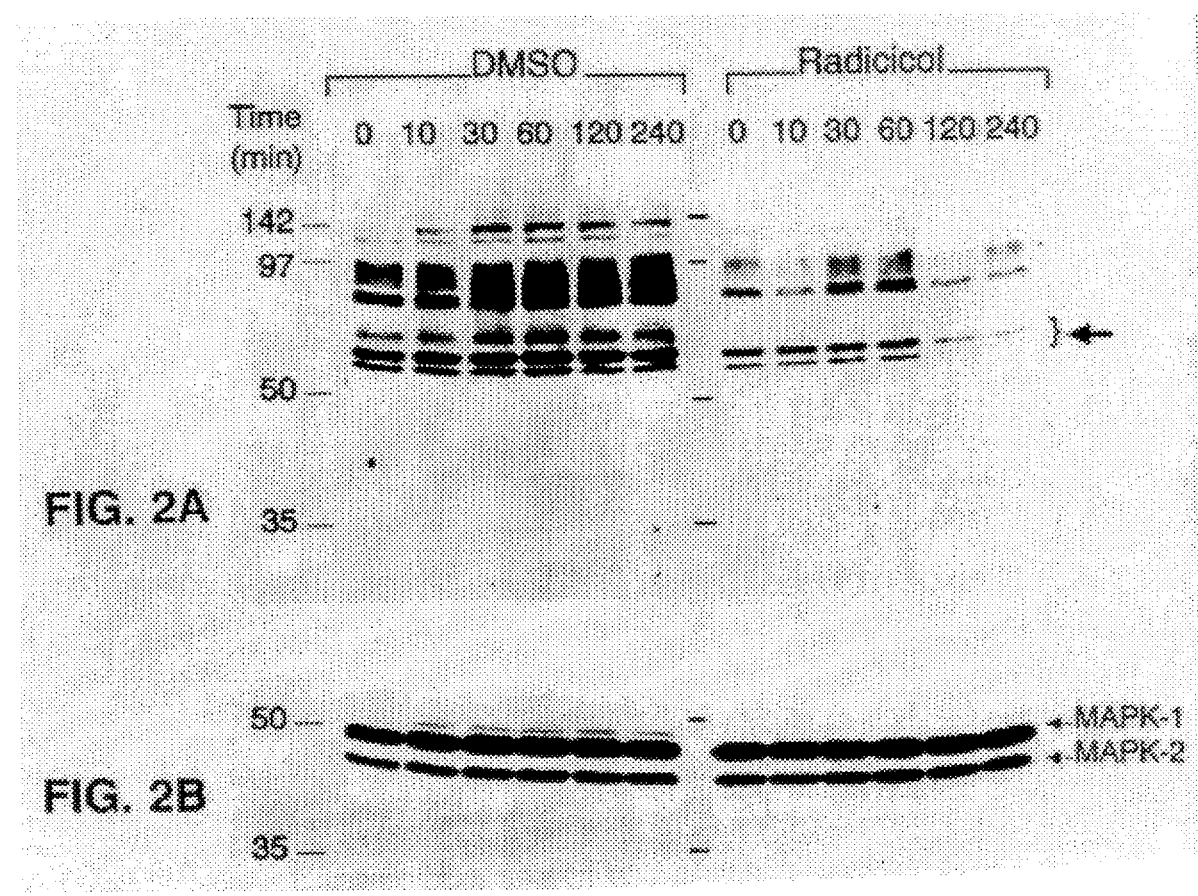

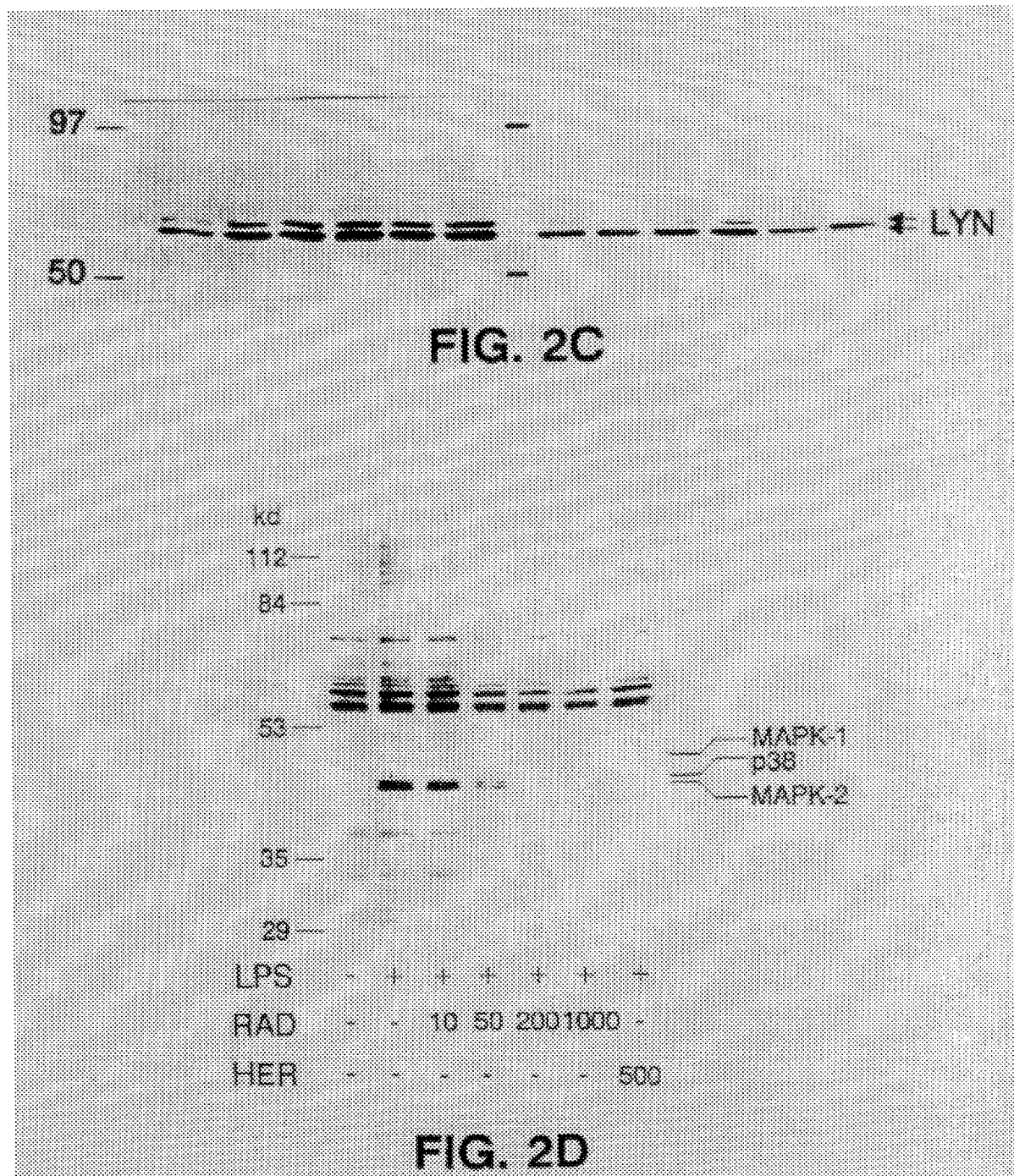

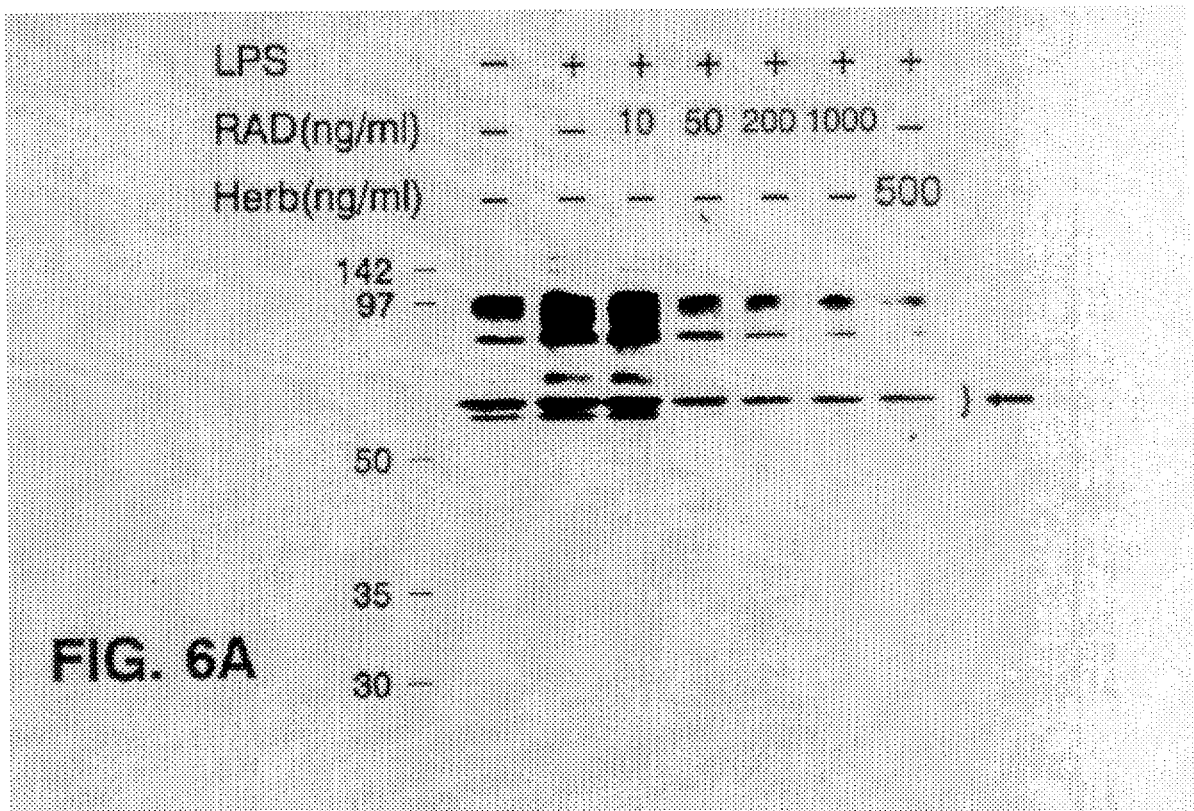
FIG. 6A
FIG. 6B
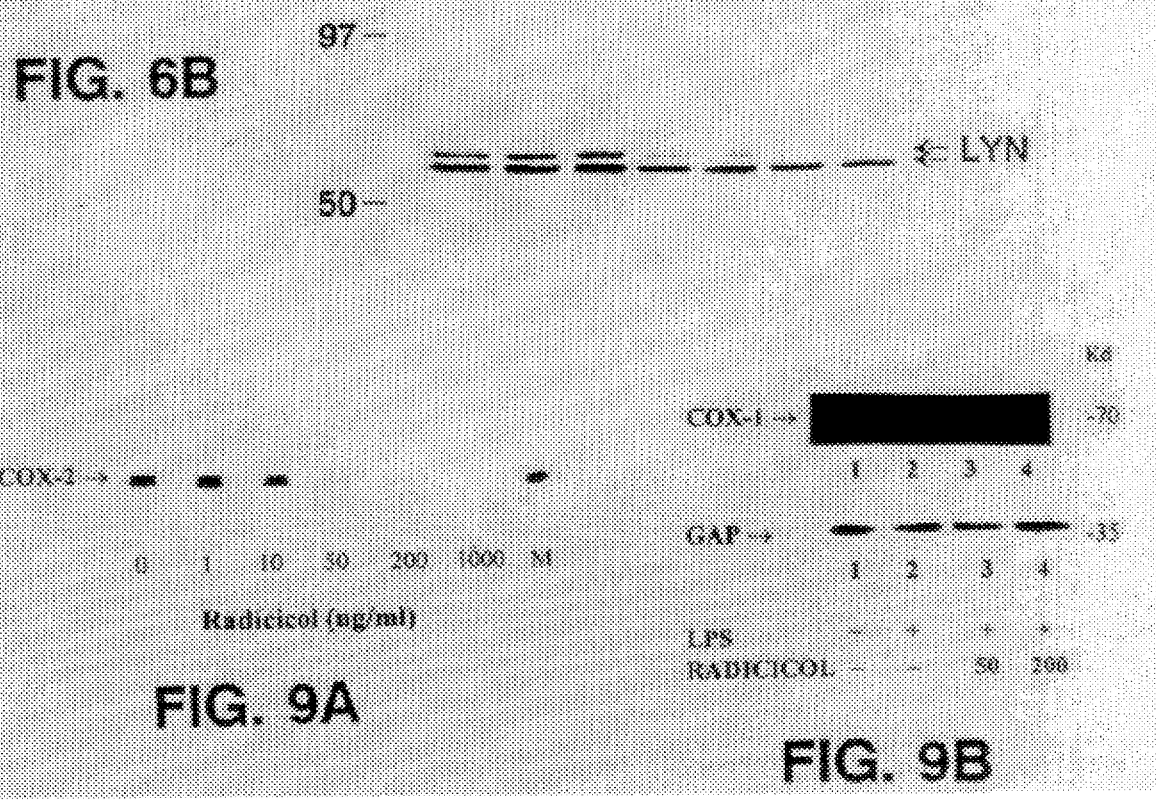
FIG. 9A
FIG. 9B

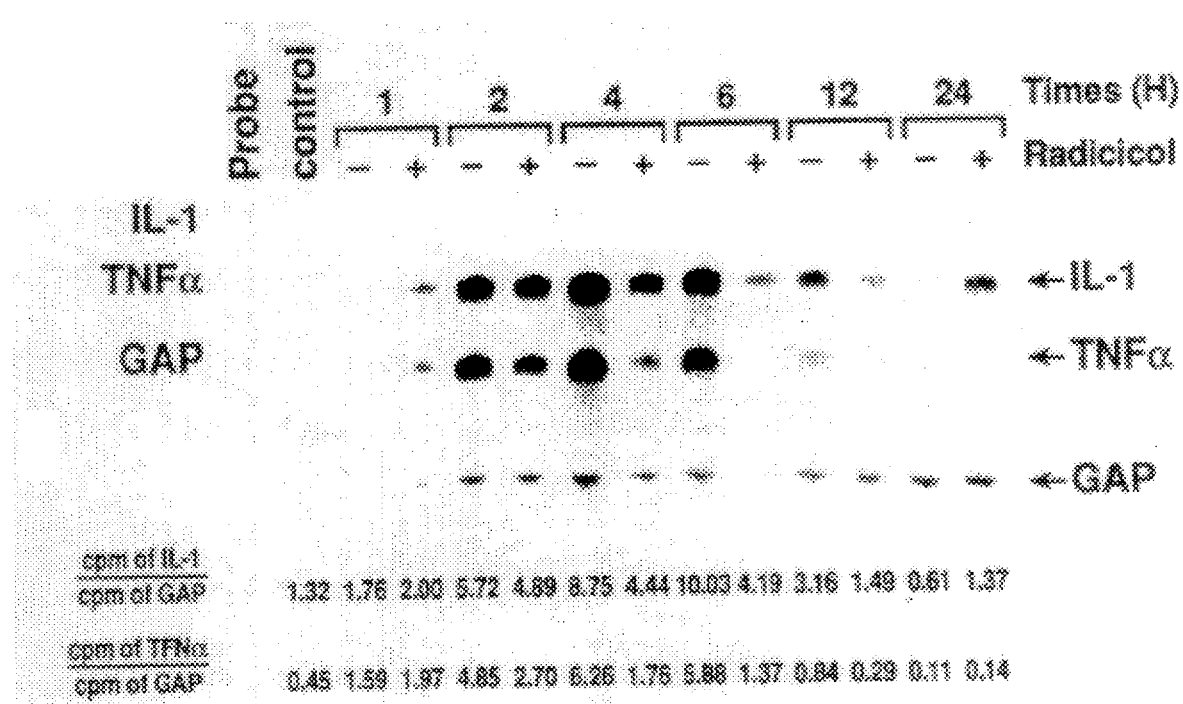
FIG. 14
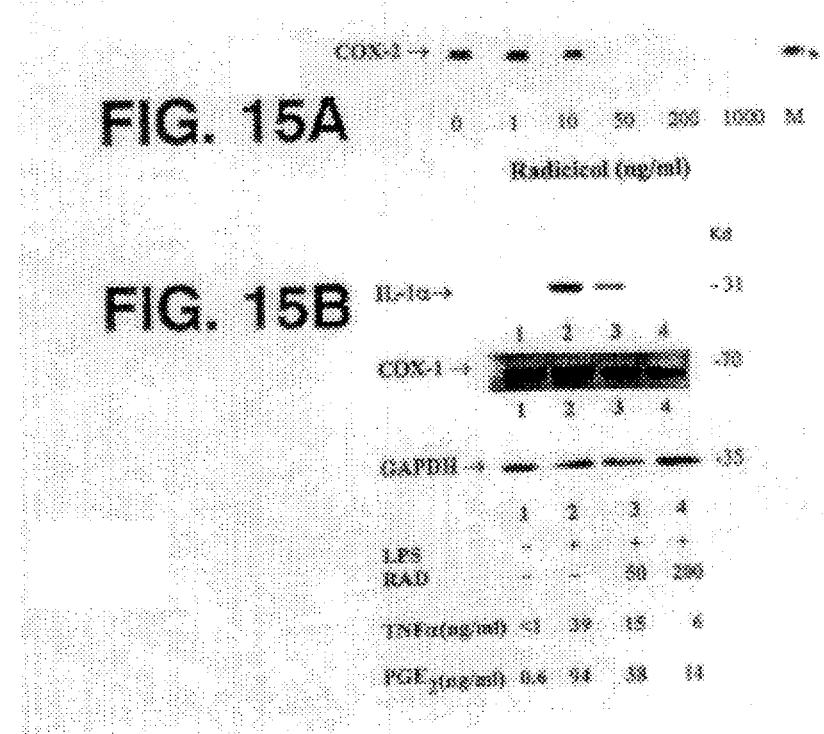
FIG. 15A
FIG. 15B

METHOD OF USE OF RADICICOL FOR TREATMENT OF IMMUNOPATHOLOGICAL DISORDERS

BACKGROUND OF THE INVENTION

1. Field of the Invention

This invention relates generally to the compound, radicicol, and specifically to the use of radicicol for the treatment of inflammation and endotoxemia-associated disorders.

2. Description of Related Art

Inflammation is a protective reaction against a variety of exogenous (microbial, chemical, physical) or endogenous (immunological, neurological) disturbances, which is characterized by the accumulation and activation of leukocytes in the affected tissue. Depending on the cause, inflammation can resolve rapidly or develop into a complex process involving different leukocytes, as well as endothelial and mesenchymal cells. These cells interact by means of mediators such as cytokines and growth factors. The histology of inflamed sites can differ markedly. The acute infiltrate in common bacterial infections, or after local deposition of IgG immune complexes is mainly neutrophilic, whereas mononuclear cells predominate in infections by intracellular pathogens, and in delayed-type hypersensitivity. By contrast, eosinophil and basophil leukocytes are prominent in inflammatory reactions that follow immediate-type allergy, certain parasitic infestations and autoimmune events.

Lipopolysaccharide (LPS) is intimately involved in the induction of the sepsis syndrome, including septic shock, systemic inflammatory response syndrome, and multiorgan failure. Sepsis is a morbid condition induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, acute respiratory distress syndrome and multiple organ failure.

LPS, or endotoxin, is a toxic component found in the outer membrane of all gram-negative microorganisms (e.g., *Escherichia coli, Klebsiella pneumonia, Pseudomonas aeruginosa*). It has been determined that LPS is a potent and pleiotropic stimulus for immune cells, both in vitro and in vivo (Morrison, D. C. & J. L. Ryan, *Annu. Rev. Med.*, 38:417, 1987; Bone, R. C., *Ann. Intern. Med.*, 115:457, 1991). Compelling evidence supports the toxic role of LPS in that all of the pathophysiological effects noted in humans during gram-negative sepsis can be completely duplicated with purified LPS. The mechanism by which this toxic component activates responsive cells is complex and not fully understood. The host response to gram-negative bacterial infection is dependent upon effector cell recognition of these bacteria and/or LPS and involves serum proteins and cell membrane receptors. While the clearance of bacteria and LPS is via endocytosis and phagocytosis by reticuloendothial cells, concomitant activation of the host immune response by LPS results in secretion of cytokines by activated macrophages which can trigger the exaggerated host responses that occur during gram-negative bacterial infection.

The discovery of a serum protein, identified as LPS binding protein (LBP), that exhibits high affinity binding to LPS ($K_d \approx 10^{-9}$ $M^{-1}$), helped to define the fate of LPS once released in vivo (Tobias, et al. (*J. Exp. Med.*, 164:777, 1986)). It was demonstrated that this novel protein, with a molecular weight of 60 kD, which is synthesized in the liver is an acute phase serum protein reaching levels of 200 μg/ml in humans. The formation of high affinity LPS/LBP complexes is followed by recognition by macrophages with subsequent release of tumor necrosis factor-alpha (TNF-α) and other macrophage secretory products (Schumann, R. R., et al., *Science*, 249:1429, 1990).

TNF-α and interleukin-1 (IL-1) are polypeptide cytokines which are principally produced by monocytes and macrophages and play a prominent role in the inflammatory response. When released by activated immune cells, these cytokines can increase expression of adhesion molecules on neutrophils and endothelial cells (promoting adhesion of leukocytes thereto), stimulate production of vasodilating prostoglandins, stimulate production of chemotactic factors (e.g., IL-8), stimulate neutrophils and activate fibroblasts. Additionally, fibroblast proliferation in response to cell injury is stimulated by platelet derived growth factor (PDGF) and fibroblast growth factor (FGF).

The response to cell injury mediated by these regulatory cytokines is usually beneficial to a host, resulting in the formation of new blood vessels and scar tissue at the site of injury. However, excessive inflammation and fibrosis is implicated in many pathological states, including asthma, coronary restenosis, autoimmune diseases (such as rheumatoid arthritis), and cirrhosis. Other important cytokines and chemokines and other proteins which are pro-inflammatory agents include interferon gamma (IFN-γ), interleukin-6 (IL-6), macrophage chemotactic protein (MCP), inducible nitric oxide synthetase (iNOS), mitogen activated protein kinases (MAPK), macrophage inflammatory protein, KC/CINC (growth related gene) tissue factor (TF), granulocyte-macrophage-colony stimulating factor (GM-CSF) and phosphotyrosine phosphatase (PTPase).

A wide variety of human diseases are associated with inflammation. These range from acute appendicitis to asthma, myocardial infarction, specific immunological disease processes, infection with viruses or bacteria, malignancy and metastasis, endotoxemia and reperfusion injury.

Cyclooxygenase (COX; prostaglandin endoperoxide synthase, EC) catalyzes the conversion of arachidonic acid to prostaglandin (PG) endoperoxide (PGH2). This is the rate limiting step in PG and thromboxane biosynthesis. Two isoforms of COX have been cloned from animal cells including constituitively expressed COX-1 (DeWitt, D. L., and Smith, W. L., *Proc. Natl. Acad Sci., USA*, 85:1412–1416, 1988; Merlie, et al., *J. Biol. Chem.*, 263:3550–3553, 1988; Yokoyama, et al., *FEBS Lett.*, 231:347–351, 1988; DeWitt, et al., *J. Biol. Chem.*, 265:5192–5198, 1990; and Yokoyama, C. and Tanabe, T., *Biochem. Biophys. Res. Commun.*, 165:888–894, 1989) and mitogen-inducible COX-2 (Xie, et al., *Proc. Natl. Acad. Sci., USA*, 88:2692–2696, 1991; Kujubu, et al., *J. Biol. Chem.*, 266:12866–12872, 1991; O'Banion, et al., *J. Biol. Chem.*, 266:23261–23267, 1991; Hla, T. and Nielson, K., *Proc. Natl. Acad Sci., USA*, 89:7384–7388, 1992; Jones, et al., *J. Biol. Chem.*, 268:9049–9054, 1993; and Feng, et al., *Arch. Biochem. Biophys.*, 307:361–368, 1993). Prostaglandins produced as a result of the activation of COX-1 may have some physiological functions, such as the antithrombogenic action of prostacyclin released by the vascular endothelium, and cytoprotective effect of PGs produced by the gastric mucosa (Whittle, et al., *Nature*, 284:271–273, 1980). COX-2 is expressed following the activation of cells by various pro-inflammatory agents including cytokines (Hla, T., and Neilson, K., supra, 1992; Feng, et al., supra, 1993), endotoxin (Lee, et al., *J. Biol. Chem.*, 267:25934–25938, 1992) and other mitogens (Kujubu, et al., supra, 1991; O'Banion, et al., supra, 1991; and Hla, T., and Neilson, K., supra, 1992). These observations lead to the suggestion that COX-2 instead of COX-1 may be responsible for producing prostanoids involved in inflammation and/or mitogenesis.

Neoplastic transformation of chicken embryo fibroblasts by Rous sarcoma virus results in the activation of a set of early response genes encoding growth factors and transcription factors involved in the regulation of cell division (Simmons, et al., *Proc. Natl. Acad. Sci., USA*, 86:1178–1182, 1989; and Bedard, et al., *Proc. Natl. Acad. Sci., USA*, 84:6715–6719, 1987). One of these genes encodes the mitogen inducible cyclooxygenase (COX-2). Induction of these genes is dependent on the activity of the Vsrc oncogene product $p60^{v-src}$, a tyrosine kinase. In addition, it has been shown that LPS rapidly increases protein tyrosine phosphorylation in macrophages, and that the early signalling event appears to mediate some downstream macrophage responses to LPS (Stefanova, et al., *J. Biol. Chem.*, 268:20725–20728, 1993; Weinsein, et al., *Proc. Natl. Acad. Sci., USA*, 88:4148–4152, 1991; and Han, et al., *J. Biol. Chem.*, 268:25009–25014, 1993). Radicicol, a fungal antibiotic with a macrocyclic ring structure, was reported as an inhibitor of $p60^{v-src}$ (Kwon, et al., *Cancer Res.*, 52:6926–6930, 1992).

Radicicol, 5-chloro-6-(7,8-epoxy-10-hydroxy-2-oxo-3,5-undecadienyl)-β-resorcyclic acid μ-lactone, also known as monorden, is an antibiotic substance isolated from several microorganisms including *Monosporium bonarden* (Delmotte-Plaque, *Nature*, 171:344, 1953). The structural formula, physical, chemical and other properties are given in the Merck Index, 11th Edition, compound 6163) and has been described by Mirrington, et al., *(Tetrahedron Letters*, 7:365, 1963). Radicicol was known to be an antibiotic and to have a strong inhibitory effect in vitro on the growth of tumor cells (U.S. Pat. Nos. 3,428,526 and 4,228,079).

Other than glucocorticoids, pharmacological agents that suppress the expression of COX-2 without affecting COX-1 have not been identified (Lee, et al., supra, 1992; Vane, J., *Nature*, 367:215–216, 1994; and Kujubu, D. A., and Herschman, H. R., *J. Biol. Chem.*, 267:7991–7994, 1992). Therefore, there is a need to identify compounds which selectively inhibit COX-2 expression and which are potent anti-inflammatory agents, but which present minimum side effects. Such a compound should preferably inhibit the production of a wide variety of proinflammatory cytokines, chemokines and other proteins.

SUMMARY OF THE INVENTION

The present invention is based on the discovery that the fungal antibiotic, radicicol, is effective for treatment of inflammation and endotoxin-related disorders. Radicicol inhibits the production of prostanoids and proinflammatory cytokines by suppressing expression of mitogen-inducible cyclooxygenase and proinflammatory cytokine genes, for example. The present invention provides a method of treating an immunopathological disorder in a subject comprising administering to the subject with the disorder, a therapeutically effective amount of radicicol or functional derivative thereof. Immunopathological disorders which may be treated by the method of the invention include those associated with expression of COX-2, IL-1, and/or TNF-α and those associated with tyrosine phosphorylation.

BRIEF DESCRIPTION OF THE DRAWINGS

FIG. 2 shows a time course of protein tyrosine phosphorylation and its inhibition by radicicol in LPS-stimulated macrophages. FIG. 2A shows the results of cells that were pretreated with radicicol (200 ng/ml) for 4 hours, and then stimulated with LPS (10 μg/ml) containing radicicol or vehicle, DMSO (5 μl/ml) for various time periods indicated. Solubilized proteins were analyzed by antiphosphotyrosine immunoblotting. Molecular size markers run on the center lane between DMSO and radicicol lanes are shown on the left. An arrow on the right indicates tyrosine phosphorylated protein bands superimposed with $p53/56^{byn}$ bands, shown below.

FIG. 2B shows the same membrane as in FIG. 2A after being stripped and reprobed with polyclonal anti-MAPK antibodies recognizing both MAPK-1 and MAPK-2. The time scale is the same as for 2A.

FIG. 2C shows the same membrane as in FIG. 2A after being stripped and reprobed with polyclonal anti-$p53/56^{byn}$ antibodies. The time scale is the same as for 2A.

FIG. 2D shows inhibition of tyrosine phosphorylation of mitogen activated protein kinases by radicicol in RAW 264.7 cells. Antiphosphotyrosine immunoblots were as described for FIG. 2A. MAPK-1, MAPK-2 and p38 (Han, et al., *Science*, 265:808, 1994) are shown.

FIG. 6 shows a dose response by radicicol in inhibiting protein tyrosine kinase in LPS-stimulated macrophages. FIG. 6A shows an immunoblot after cells were pretreated with radicicol or herbimycin at the indicated concentrations for 4 hours, and then stimulated with LPS (10 μg/ml) containing radicicol or herbimycin A. The control was pretreated with vehicle, DMSO (5 μl/ml) only. An arrow on the right indicates tyrosine phosphorylated protein bands superimposed with $p53/56^{byn}$ bands shown below. Rad, radicicol; Herb, herbimycin A. Molecular size markers are shown in kilodaltons. FIG. 6B shows a Western blot analysis of p53/56$^{lyn}$ in the same samples used in FIG. 6A as described in FIG. 2C. LYN, p53/56$^{lyn}$.

FIG. 9 shows the effects of radicicol on expression of COX-2, COX-1 and glyceraldehyde-3-phosphate dehydrogenase (GAP). FIG. 9A shows rat alveolar macrophage lysates preincubated with LPS (10 µg/ml) and various concentrations of radicicol. Samples were immunoprecipitated with COX-2 antibodies and subjected to SDS-polyacrylamide gel electrophoresis and fluorography. FIG. 9B shows a Western blot analysis of rat alveolar macrophage lysates incubated in RPMI with 3% serum for 16 hours with or without LPS and/or radicicol. Microsomes from lysed cells were used for COX-1 and whole lysate was used for GAP. Lane 1, cells incubated without LPS and radicicol; Lane 2, cells incubated with LPS (10 µg/ml) only; Lane 3, cells incubated with LPS and radicicol (50 ng/ml); Lane 4, cells incubated with LPS and radicicol (200 ng/ml).

FIG. 14 shows a time course for levels of mRNA for IL-1, TNF-α and glyceraldehyde-3-phosphate dehydrogenase (GAP) in LPS-treated macrophages in the presence or absence of radicicol (as described in FIG. 10).

FIG. 15 shows the effects of radicicol on expression of COX-2, COX-1, IL-1 and glyceraldehyde-3-phosphate dehydrogenase (GAP). FIG. 15A shows rat alveolar macrophage lysates preincubated with LPS (10 µg/ml) and various concentrations of radicicol. Samples were immunoprecipitated with COX-2 antibodies and subjected to SDS-polyacrylamide gel electrophoresis and fluorogaphy. FIG. 15B shows a Western blot analysis of rat alveolar macrophage lysates incubated in RPMI with 3% serum for 16 hours with or without LPS and/or radicicol. Microsomes from lysed cells were used for COX-1 and whole lysate was used for GAP. Lane 1, cells incubated without LPS and radicicol; Lane 2, cells incubated with LPS (10 µg/ml) only; Lane 3, cells incubated with LPS and radicicol (50 ng/ml); Lane 4, cells incubated with LPS and radicicol (200 ng/ml). TNF-α and PGE2 were measured by radioimmunoassay of the supernatant.

DETAILED DESCRIPTION OF THE INVENTION

Figure 1:
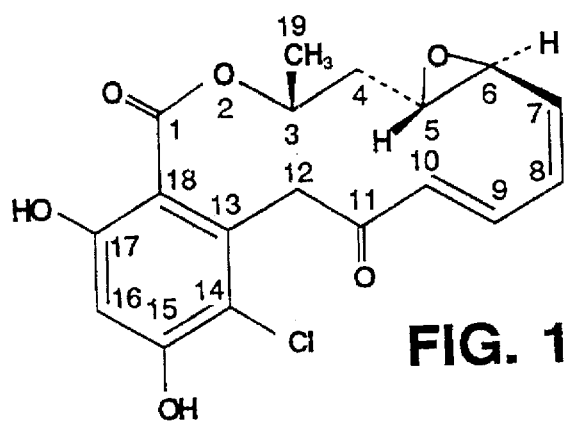
FIG. 1 shows chemical structure of radicicol.

The present invention is provides a new method of use for the compound known as monorden, or radicicol. As described herein, radicicol effectively inhibits proinflammatory agents including cytokines, endotoxin and other mitogens as well as protein tyrosine kinases.

In a preferred embodiment, the present invention provides a method of treating an immunopathological disorder in a subject comprising administering to the subject with the disorder, a therapeutically effective amount of radicicol or functional derivative thereof.

Radicicol of the present invention refers to a compound with the formula (I) and their salts:

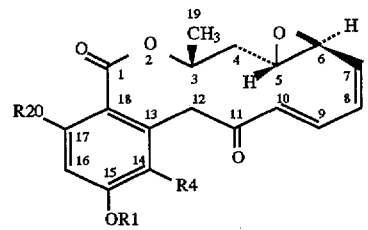

where R1 and R2 are independently H or —COR3; R3 is H, 1–50C alkyl, 1–20C alkoxy, 2–30C alkenyl, 2–30C alkenyloxy, 2–10 alkynyl, 6–14C aryl or aryloxy, a 5–6 membered heterocycle (containing 1–3 N, O and/or S heteroatoms and optionally fused to an aryl group), 3–8C cycloalkyl (optionally fused to aryl) or 5–8C cycloalkenyl. All groups may be substituted. R4 is preferably chloride, however, any halogen atom can be substituted at this position.

When used herein, the term radicicol refers to formula I and functional analogs, derivatives, and isomers thereof, which are capable of modulating an inflammatory or endotoxic response as described herein. It is also envisioned that radicicol and any homolg, analog, isomer or derivative can be used in various combinations or mixtures in the method of the invention.

The compounds used in the method of the invention may contain asymmetric carbon atoms and/or carbon-carbon double bonds and can, therefore, form optical and/or cis/trans isomers. Although these are all referred to herein by a single formula, the present invention envisages both mixtures of the isomer and the individual isolated isomers (which may be prepared by stereospecific synthesis techniques or by separation of a synthesized mixture using conventional methods).

Examples of compounds used in the method of the invention are those of formula I, above, in which R1 and R2 may be defined as follows, but are not limited acetyl, allyloxycarbonyl, benzoyl, butyl, cyclobutyl, butyryl, benzyl, carbamoyl, decanoyl, dodecyl, ethyl, ethoxycarbonyl, fluoenylmechoxycarbonyl, furyl, cyclohexeny, cycloheptyl, heptanoyl, hexyl, cyclohexyl, hexanoyl, indolyl, isoxazolyl, methly, methoxycarbonyl, methoxyethoxymethyl, methoxymethyl, morpholino, naphthyl, octyl, cyclooctyl, cyclopentenyl, phenyl, peperidyl, peperazinyl, pentyl, cyclopentyl, propyl, cyclopropyl, propionyl, pyridyl, pyrrolidinyl, retinoyl, thienyl, thiazolyl, and trichloroethoxycarbonyl.

Radicicol is administered by any suitable means, including parenteral, subcutaneous, intrapulmonary, and intranasal administration. Parenteral infusions include intramuscular, intravenous, intraarterial, or intraperitoneal administration. Radicicol may also be administered transdermally in the form of a slow-release subcutaneous implant for example, or orally in the form of capsules, powders or granules. Radicicol can also be admistered by inhalation. For example, when used therapeutically for treatment of an inflammatory disorder of the lungs, a preferred route of administration would be by a pulmonary aerosol.

Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention provides any pharmaceutical preparations and compositions containing the radicicol of the invention for use in the method of the invention. The form will vary depending upon the route of administration. For example, compositions for injection can be provided in the form of an ampule, each containing a unit dose amount, or in the form of a container containing multiple doses.

Radicicol can be formulated into the therapeutic composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the radicicol may be controlled by altering the concentration of the macromolecule.

Another method for controlling the duration of action comprises incorporating the radicicol into particles of a polymeric substance such as polyesters, polyamino acids, hydrogels, polylactide/glycolide copolymers, or ethylenevinylacetate copolymers. Alternatively, it is possible to entrap radicicol in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The dosage range for administration of radicicol will vary depending on the age, sex, and physical condition of the subject. Radicicol is administered from about 1 to about 100 µg\100 g\dose, preferably from about 1 to about 50 µg\100 g\dose, and most preferably from about 1 to about 20 µg\100 g\dose.

An immunopathological disorder treated by the method of the invention may be associated with COX-2 expression and/or associated with cytokines or other proinflammatory agents such as, TNF, IL-1, COX-2, MAPKs, IFNγ, MCP-1, iNOS, MIP-2, KC, TF, PTPase, IL-6 or GM-CSF production, for example. The method comprises administering to the subject a therapeutically effective amount of radicicol. The term "immunopathological disorder" refers to any disease which involves the immune response or immunity in general. An immunopathological disorder treated by the method of the invention is typically identified by production of one or more proinflammatory agents (e.g., proteins, enzymes). As used herein, a "proinflammatory agent" is a cytokine, chemotactic agent (chemokine), enzyme, or the like, which plays a role in the inflammatory response. Examples of proinflammatory agents include TNF-α, interleukins, (e.g., IL-1, IL-6), IFN-γ, COX-2, MAPKs, MCP, iNOS, MIP, KC/CINC, TF and PTPase. Other proinflammatory agents will be known to those of skill in the art.

"Therapeutically effective" as used herein, refers to that amount of inhibitor that is of sufficient quantity to ameliorate the cause of the immunopathological disorder. "Ameliorate" refers to a lessening of the detrimental effect of the disorder in the patient receiving the therapy. The subject of the invention is preferably a human, however, it can be envisioned that any animal with an immunopathological disorder can be treated by the method of the invention, for example, a SCID mouse grafted with human bone marrow (humanized SCID). Examples of immunopathological disorders which can be treated by the method of the invention include acquired immunodeficiency disorder (AIDS), toxic shock syndrome, allograft rejection, ultraviolet and radiation responses, and disorders associated with the activation of T cells, B cells and macrophages during the immune response and the acute phase response and disorders associated with advanced cancer such as tumor necrosis factor-mediated cachexia.

The invention provides a method of treating or ameliorating an immunopathological disorder such as endotoxemia or septic shock (sepsis), or one or more of the symptoms of sepsis comprising administering to a subject displaying symptoms of sepsis or at risk for developing sepsis, a therapeutically effective amount of radicicol. The term "ameliorate" refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza B, Neisseria meningitides,* staphylococci, or pneumococci. Patients at risk for sepsis include those suffering from burns, gunshot wounds, renal or hepatic failure, trauma, burns, immunocompromised (HIV), hematopoietic neoplasias, multiple myeloma, Castleman's disease or cardiac myxoma.

The term "therapeutically effective amount" as used herein for treatment of endotoxemia refers to the amount of radicicol used is of sufficient quantity to decrease the subject's response to LPS and decrease the symptoms of sepsis. The term "therapeutically effective" therefore includes that the amount of radicicol sufficient to prevent, and preferably reduce by at least 50%, and more preferably sufficient to reduce by 90%, a clinically significant increase in the plasma level of TNF. The dosage ranges for the administration of radicicol are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. An decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of radicicol, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature,* 330:662, 1987).

A patient who exhibits the symptoms of sepsis may be treated with an antibiotic in addition to the treatment with radicicol. Typical antibiotics include an aminoglycoside, such as gentamycin or a beta-lactam such as penicillin, or cephalosporin. Therefore, a preferred therapeutic method of the invention includes administering a therapeutically effective amount of radicicol substantially simultaneously with administration of a bactericidal amount of an antibiotic. Preferably, administration of radicicol occurs within about 48 hours and preferably within about 2–8 hours, and most preferably, substantially concurrently with administration of the antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Administration of a radicicol compound in the method of the invention may also be used for ameliorating post-reperfusion injury. When treating arterial thrombosis, induction of reperfusion by clot lysing agents such as tissue plasminogen activator (t-PA) is often associated with tissue damage. Such tissue damage is thought to be mediated at least in part by leukocytes including but not limited to polymorphonuclear leukocytes (PMN). Therefore administration of the radicicol would block leukocyte or PMN-endothelial interactions, and thereby diminish or prevent post-reperfusion injury.

The method of the invention is also useful for treatment of inflammation due to allergic or autoimmune disorders. Examples of allergic disorders include allergic rhinitis, asthma, atopic dermatitis, and food allergies. Examples of autoimmune disorders, where the immune system attacks the host's own tissues, include, but are not limited to, type 1 insulin-dependent diabetes mellitus, inflammatory bowel disease, dermatitis, meningitis, thrombotic thrombocytopenic purpura, Sjögren's syndrome, encephalitis, uveitic, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, acquired immune deficiency syndrome, septic shock and other types of acute inflammation, and lipid histiocytosis. Essentially, any disorder which is etiologically linked to the pro-inflammatory process (e.g., induction of IL-1, TNF-$\alpha$, COX-2 expression) would be considered susceptible to treatment.

The method of the invention is also useful for the treatment of microbial infections. Many microbes, such as bacteria, rickettsia, various parasites, and viruses, bind to vascular endothelium and leukocytes, and induce an inflammatory reaction resulting in production of IL-1 and IL-2 for example. Thus, radicicol used in the method of the invention may be administered to a patient to prevent inflammation associated with such infections.

The method of the invention may also be useful for treating an immunopathological disorder associated an oncogene having tyrosine kinase activity. Preferably, the disorder is associated with a Src family tyrosine kinase. For example, a disorder assoiciated with overexpression of c-src, c-fyn, p56lyn, c-abl, lsk/tck, hck or c-fins.

While not wanting to be bound by a particular theory, the present invention indicates that radicicol suppresses tyrosine phosphorylation of these kinases and that inhibition of COX-2 expression by radicicol is at least in part mediated by the inhibition of protein-tyrosine kinases.

The effectiveness of treatment using the method of the invention can be monitored by common detection methods used in the art, such as immunoassays, Northern and Western blot analysis and RNase protection assays. Examples of types of immunoassays which can be utilized to detect and monitor levels of cytokines, chemokines, mitogens, or other proteins affected by radicicol in a sample, include competitive and non-competitive immunoassays in either a direct or indirect format. Examples of such immunoassays are the radioimmunoassay (RIA) and the sandwich (immunometric) assay. Detection of the protein can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules can be bound by adsorption from an aqueous medium, although other modes of affixation, such as covalent coupling or other well known means of affixation to the solid matrix can be used. Preferably, the first antibody molecule is bound to a support before forming an immunocomplex with antigen (e.g., cytokine), however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody-containing solid support at protein binding sites on the surface that are not occupied by the antibody molecule.

A typical aqueous protein solution contains about 2–10 weight percent bovine serum albumin in PBS at a pH of about 7–8. The aqueous protein solution-solid support mixture is typically maintained for a time period of at least one hour at a temperature of about 4°–37° C. and the resulting solid phase is thereafter rinsed free of unbound protein.

The first antibody can be bound to many different carriers and used to detect a cytokine or other protein in a sample. Examples of well-known carriers include grass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies or antigen, or will be able to ascertain such, using routine experimentation.

In addition, if desirable, an antibody for detection in these immunoassays can be detectably labeled in various ways. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will known of other suitable labels for binding to the monoclonal antibodies of the invention, or will be able to ascertain such, using routine experimentation. Furthermore, the binding of these labels to the antibodies used in the method of the invention can be done using standard techniques common to those of ordinary skill in the art.

In addition, one of skill in the art can monitor the effect of radicicol on a protein kinase by measuring the effect on the activity of the kinase. Such a method may comprise incubating the components, which include the kinase or a polynucleotide encoding the kinase and its substrate (e.g., Src tyrosine kinase and $p53/56^{lyn}$), under conditions sufficient to allow the components to interact, then subsequently measuring the effect the composition has on kinase activity. For example, the increase or decrease of kinase activity can be measured by adding a radioactive compound to the mixture of components, such as $^{32}$P-ATP, and observing radioactive incorporation into the substrate to determine whether the compound inhibits, stimulates or has no effect on protein kinase activity. A polynucleotide encoding the kinase may be inserted into an expression vector and the effect of a composition on transcription of the kinase or stability of the mRNA can be measured, for example, by Northern blot analysis or RNase protection assay (see for example, Current Protocols in Molecular Biology, Ausubel, et al., *Wiley Interscience*, 1994, incorporated herein by reference). The level of cytokine, chemokine, mitogen or other radicicol inhibited protein described herein can also be monitored by these and other standard molecular biology techniques known to those of skill in the art and described herein.

The following examples are intended to illustrate but not limit the invention. While they are typical of those that might be used, other procedures known to those skilled in the art may alternatively be used.

EXAMPLE 1

MATERIALS AND METHODS

1. Preparation of radicicol

Radicicol was prepared from the culture broth of a fungus strain KF9 (ATCC, Rockville, Md.), according to the procedure described previously (Kwon, et al., *Cancer Res.*, 52:6926, 1992) and obtained from Dr. Beppu, Tokyo University. Briefly, the active compound was extracted with acetone from the wet cultured cells of KF9 and was chromatographed on a silica gel column chromatography (Merk, Kieselgel 60, 3×15 cm) eluted with $CHCl_3$-methanol (99:1, v/v). The active fractions were collected and concentrated in vacuo to give a crude crystalline substance. This was recrystallized from benzene to yield pure colorless needles, mp 194° C. The molecular formula of radicicol was $C_{18}H_{17}ClO_6$ as determined by electron impact and fast atom bombardment-mass spectrometry (MS) analysis (MS m/z 364.782); $[\alpha]D+195°$ (c=0.4, $CHCl_3$),IR (KBr disc): 3500, 1665, 1606cm$^{-1}$; UV (methanol) $\lambda_{max}$:265 ($\epsilon$ 13,400), 315 ($\epsilon$ 2,800); $^1$H NMR (CDCl$_3$) σ:1.52 (d, J=6.5 Hz, 3H), 2.07 (m, J=15 Hz, 1H), 2.43 (dd, J=15 HZ, 1H), 2.96 (dd, J=2.8, 3.2, 8.5 Hz, 1H), 3.18 (s, 1H), 3.97 (d, J=16 Hz, 2H), 4.81 (d, J=16 Hz, 2H), 5.35 (m, J=6.5 Hz, 1H), 5.84 (dd, J=2, 5, 11 Hz, 1H), 6.08 (m, J=16 Hz, 1H),6.19(d,J=8, 11 hz, 1H),6.7 (s, 1H),7.47(dd, J=11, 16 Hz, 1H), 11.2 (s, 1H); $^{13}$C NMR (CDCl$_3$) σ 18.48 (c-19, 1), 35.89 (C-4, t), 46.27 (C-12, t), 55.33 (C-5 or 6, d), 55.56 (C-5 or 6, d), 71.45 (C-3, d), 103.67 (C-16, d), 106.94 (C-18, s), 115.58 (C-14, s), 129.64 (C-7, 8, 9 or 10, d), 130.11 (C-7, 8, 9, or 10, d), 134.70 (C-7, 8, 9 or 10, d), 136.17 (C-13, s), 139.12 (C-7, 8, 9, or 10, d), 156.60 (C-17, s), 163.24 (C-15, s), 168.88 (C-1, s), 197.29 (C-11, s). All these spectrophotometric analysis data were identical with those previously reported (Mirrington, et al., *Tetrahedron Lett.*, 7:365–370, 1964; Nozawa and Nakajima, *J. Nat. Prod*, 42(4), 374–377, 1979). Purity of radicicol was determined by comparing with authentic radicicol (kindly supplied by Dr. S. Nakajima, Hoshi College of Pharmacy Tokyo, Japan) using HPLC analysis on an Aquasil silica gel column (Senshu Co., Tokyo, Japan) with 0.5% HCOOH—CHCl$_3$. The purity of radicicol prepared as described herein was better than 99%. FIG. 1 shows the chemical structure of radicicol.

2. Preparation of cell lysates and antiphosphotyrosine immunoblotting

Attached macrophages were incubated in RPMI containing 3% FCS for 8 hours and then pretreated with various concentrations of radicicol or herbimycin A for an additional 4 hours. The media were removed and cells were stimulated with the fresh media containing LPS (10 μg/ml) and radicicol or herbimycin A for 1 hour. Stimulated cells were washed with ice cold PBS containing 1 mM Na$_3$VO$_4$ (1 mM), EDTA (5 mM), EGTA (1 mM), phenylmethylsulfonyl fluoride (1 mM), leupeptin (10 μM) and Triton X-100 (1% wt/vol) for 20 minutes on ice, then sonicated in Branson-450 sonifier. Detergent-insoluble material was removed by centrifugation (10,000×g, 20 minutes, 4° C.). Solubilized proteins were separated on 10% SDS polyacrylamide gels and transferred to nitrocellulose (6 hours, 250 mA). The nitrocellulose membrane was blocked with 3% nonfat dry milk for 2 hours at room temperature, and after rinsing twice with PBS, the membrane was incubated with murine monoclonal antiphosphotyrosine antibody (4G10, UBI, 1 μg/10 ml in PBS containing 0.1% Tween 20 and 3% nonfat dry milk) for 1 hour at room temperature with continuous shaking. After rinsing with three changes of PBS containing 0.1% Tween 20, the membrane was treated with the second antibody, goat anti-mouse 1 gG coupled to horseradish peroxidase (1 μg/10 ml in PBS containing 0.1% Tween 20 and 3% nonfat dry milk). After 1 hour, the membrane was washed four times and analyzed by enhanced chemiluminescence (ECL) detection system (Amersham Corporation).

To locate Src family kinases and mitogen-activated protein kinases (MAPK), the same membrane used for antiphosphotyrosine immunoblot was stripped in the buffer (2% SDS, 50 mM Tris-HCl, 100 mM 2-mercaptoethanol, pH 6.5 at 50° C. for 30 minutes). The stripped membrane was reprobed with polyclonal anti-MAPK antibodies (UBI, 1 μg/2 ml in PBS containing 0.1% Tween 20 and 3% nonfat dry milk) or polyclonal anti-Src family kinase antibodies (Santa Cruz, 1 μg/ml), followed by goat anti-rabbit IgG coupled to horseradish peroxidase (1 μg/10 ml). The immunoreactive protein bands were visualized by the ECL detection system.

3. Immunoprecipitation

Cell lysates containing equal amounts of protein (200 μg) were precleared with 200 μl of protein A-sepharose bead solution (20% v/v) for 30 minutes at 4° C. Precleared samples were then incubated with 5 μg of polyclonal anti-Src family tyrosine kinase antibodies (Santa Cruz) for 3 hours at 4° C. Immune complexes were captured by adding 200 μl of protein A-sepharose bead solution and incubating for 2 hours at 4° C. After centrifugation, the supernatant fraction was collected and concentrated using Centricon-10 (Amicon). The beads were washed three times, and resuspended in 80 μl of 2×Laemmli sample buffer and boiled for 5 minutes. Depleted supernatant and immunoprecipitates were resolved on a 10% SDS-polyacrylamide gel and subjected to antiphosphotyrosine immunoblot analysis as described above.

4. In vitro p60$^{c-src}$ kinase assay

The enzyme assays were carried out as described by Cheng, et al., *J. Biol. Chem.*, 267:9248–9256, 1992. Purified p60$^{c-src}$ (25 ng/5 μl, UBI) was incubated in the reaction buffer (100 mM Tris-HCl, pH 7.2; 2 mM EGTA; 125 mM MgCl$_2$; 25 mM MnCl$_2$; 0.25 mM Na$_3$VO$_4$) for 15 minutes at room temperature with p60$^{c-src}$ kinase substrate peptide (200 mM, KVEKIGEGTYGVVKK) (SEQ ID NO:1), 5 μCi of [γ-$^{32}$P] ATP (Dupont, NEN, specific activity: 3000 Ci/mmole), and various concentrations of radicicol. The reaction was stopped by adding 10 μl of 40% trichloroacetic acid to precipitate p60$^{c-src}$ kinase peptide. An aliquot (25 μl) of the reaction mixture was spotted onto a P81 cation exchange paper (Whatmann), and the paper was washed with 40 ml of 0.75% phosphoric acid twice and once with acetone. The radioactivity in the paper was measured in a scintillation counter.

5. Isolation of Macrophages

Rats (Sprague-Dawley) were kept in Duo-rio Bioclean racks (Laboratory Products) with filtered air in positive pressure to minimize exposure to airborne bacteria. Alveolar macrophages were collected by bronchoalveolar lavage as described by Chandler and Fulmer (*J. Immunol.*, 139:893–898, 1987). Cell viability as determined by trypan blue exclusion was greater than 90%. More than 95% of lavaged cells were macrophages as determined by differential counting.

6. Assay for Cyclooxygenase

Cells were allowed to adhere in the presence of aspirin (500 μM) in RPMI for 2.5 hours to inactivate endogenous COX. Cells were incubated in the medium containing 3% fetal calf serum (FCS) with or without LPS (10 μg/ml, Difco) for 16 hours. The incubation times for other cell types and agonists listed in Table 1 were selected from respective time course data. The medium was removed and the cells were incubated in the fresh medium containing arachidonic acid (30 μM) for 10 minutes to determine recovered COX activity which reflects the activity of de novo synthesized enzyme as described previously (Lee, et al., *J. Biol. Chem.*, 267:25934–25938, 1992).

Effects of radicicol on enzyme activities of COX-1 and COX-2 purified from ram seminal vesicle and sheep placenta, respectively (Cayman Chemicals) were determined by the conversion of [$^{14}$C] arachidonic acid (Dupont, specific activity, 57 mCi/mmole) to PGE$_2$ after separation by thin layer chromatography (TLC) as described by Mitchell, et al., *Proc. Natl. Acad. Sci.*, 90:11693–11697, 1993. The reaction mixture (1 ml) in 50 mM Tris buffer (pH 8.0) contained arachidonic acid (10.88 μM) together with [$^{14}$C]-arachidonic acid, glutathione (mM), epinephrine (5 mM), and hematin (1 μM). The reactions were initiated by adding the purified enzymes and incubated at 37° C. for 10 minutes. PGs were separated in TLC in a solvent of the organic phase of ethyl acetate/trimethylpentane/acetic acid/water, 110:50:20:100 (v/v). The PGE$_2$ band was identified by cold standard run side by side and visualized in an iodine tank. Radioactive PGE$_2$ bands were identified by superimposing the autoradiograph run on TLC plates and then scraped off. The radioactivity of PGE$_2$ band was determine by scintillation counting.

7. Metabolic labeling and immunoprecipitation

Cells were metabolically labeled in methionine free RPMI containing 200 µCi of [$^{35}$S] methionine (1,139 Ci/mmol), and COX-2 was immunoprecipitated with COX-2 polyclonal antibodies as described previously (Lee, et al., supra). The immunoprecipitated samples were subjected to SDS-polyacrylamide gel electrophoresis, followed by fluorography as described previously (Lee, et al., supra).

8. Western blot analysis for COX-1 protein

The protein level of COX-1 was assessed by Western blot analysis using polyclonal antibodies which were prepared against purified ram seminal vesicle cyclooxygenase (Lee, et al., supra). Polyclonal antibodies for glyceraldehyde-3-phosphate dehydrogenase (GAP) were prepared against porcine muscle GAP (Sigma) in rabbits. Levels of GAP protein were determined by Western blot analysis as internal controls for the same samples for which COX-1 protein levels were assessed. The second antibodies used were goat anti-rabbit IgG conjugated with alkaline phosphatase (1:1000, K&P Laboratories). Color development was made with alkaline phosphatase color reagents (K&P Laboratories) containing 5-bromo-4-chloro-3-indolyl phosphate and nitroblue tetrazolium in 0.1M Tris buffer.

9. RNase protection assay

Total cellular RNA was isolated by a single step method as described by Chomczynski and Sacchi (*Anal. Biochem.*, 162:156–159, 1987) and quantitated by its absorption at 260 nm. One microgram of total RNA was hybridized with 1×10$^5$ cpm of [$^{32}$p] labeled antisense riboprobes. The RNase protection assay was performed as described previously and the results were quantitated by detecting radioactivity in the band with the AMBIS Radioanalytic Imaging System (AMBIS System, San Diego, Calif.) (Feng, et al., *Arch. Biochem. Biophys.*, 307:361–368, 1993).

10. Measurement of COX mRNA and PG levels in glomeruli and whole kidney in rats with experimental glomerulonephritis (GN)

Female Lewis rats (The Scripps Research Institute Breeding Colony) weighing 170–250 g were used for these experiments. Immune glomerular injury was induced with anti-glomerular basement membrane (GBM) antibody produced as previously described (Blantz and Wilson, *J. Clin. Invest.*, 58:899–911, 1976). Enhanced COX-2 expression in this experimental GN has been shown previously (Feng, et al., *J. Am. Society of Nephrology*, No.3, 4:452, 1993). Radicicol dissolved in saline was infused into the renal artery beginning 10 minutes before the intravenous administration of anti-GBM antibody. The infusion was continued for 60 minutes to provide a dose of 10 µg/100 g body weight per minute. The same amount of vehicle was given for the same time to the control animals. The rats were sacrificed after 4 hours and 24 hours following anti-GBM antibody injection. The kidneys and glomeruli were collected at euthanasia.

These tissues were used for mRNA extraction and determination of PGE$_2$. A portion of the tissues was homogenized in 70% ethanol. After centrifugation, the supernatants were collected, dried under a stream of N$_2$, resuspended in PBS, and were subjected to Sep-Pak (Waters) purification, as described by Powell (W. S. Powell, *Methods Enzymol.*, 86:467–477, 1982). PGE$_2$ was measured by radioimmunoassay. Glomeruli were isolated by sequential sieving through #60 and #100 mesh wire screens. The glomeruli collected on the #200 mesh screen contained <10% tubular contamination. After washing with 0.9% saline, the glomeruli were homogenized in 4M guanidine isothiocyanate with a sonicator (Heat Systems-Ultrasonics, Plainview, N.Y.). The RNA was prepared by a single-step method, quantitated by its absorption at 260 nm, and then frozen at −70° C. The RNase protection assay was done as described above.

EXAMPLE 2

RADICICOL INHIBITS TYROSINE PHOSPHORYLATION IN LPS-STIMULATED MACROPHAGES AND OF Src FAMILY TYROSINE KINASES AND INHIBITS MITOGEN ACTIVATED KINASES

FIG. 2 shows a time course of protein tyrosine phosphorylation and its inhibition by radicicol in LPS-stimulated macrophages. FIG. 2A shows the results of cells that were pretreated with radicicol (200 ng/ml) for 4 hours, and then stimulated with LPS (10 µg/ml) containing radicicol or vehicle, DMSO (5 µl/ml) for various time periods indicated. Solubilized proteins were analyzed by antiphosphotyrosine immunoblotting. Molecular size markers run on the center lane between DMSO and radicicol lanes are shown on the left. An arrow on the right indicates tyrosine phosphorylated protein bands superimposed with p53/56$^{lyn}$ bands, shown below.

FIG. 2B shows the same membrane as in FIG. 2A after being stripped and reprobed with polyclonal anti-MAPK antibodies (UBI) recognizing both MAPK-1 and MAPK-2. The time scale is the same as for 2A. FIG. 2C shows the same membrane as in FIG. 2A after being stripped and reprobed with polyclonal anti-p53/56$^{lyn}$ antibodies. The time scale is the same as for 2A.

The time course of protein tyrosine phosphorylation in LPS-stimulated macrophages showed that the maximum phosphorylation occurred within 1 hour whether cells were treated with radicicol or not (FIG. 2A). Both MAPK-1 (42 KD) and MAPK-2 (44 KD) were detected in cell lysates derived from the time course study as determined by Western blot analysis using polyclonal anti-rat MAP kinase antibodies recognizing both MAPK-1 and MAPK-2 (FIG. 2B). However, these MAP kinases did not appear to be tyrosine phosphorylated significantly at the incubation conditions used in our studies (FIG. 2A). Tyrosine phosphorylated MAPKs were not detected by the anti-phosphotyrosine immunoblot procedure described herein. When 2% BSA, instead of 3% dry milk was utilized in the blocking buffer, tyrosine phosphorylated MAPKs were detectable as shown in FIG. 2D. FIG. 2D shows the inhibition of tyrosine phosphorylation of mitogen activated protein kinases by radicicol in macrophage cell line (RAW 264.7, ATCC). Cells were pretreated with the indicated concentrations of radicicol for four hours, and then stimulated with LPS (1 µg/ml). Solubilized proteins were analyzed by antiphosphotyrosine immunoblotting as described in FIG. 2A. Tyrosine phosphorylated MAPK bands were identified using polyclonal antibodies recognizing both MAPK-1 and MAPK-2, and polyclonal antibodies for p38. p38 is recently cloned isoform of MAPK (Han, et al., *Science*, 265:808, 1994).

Figure 3:
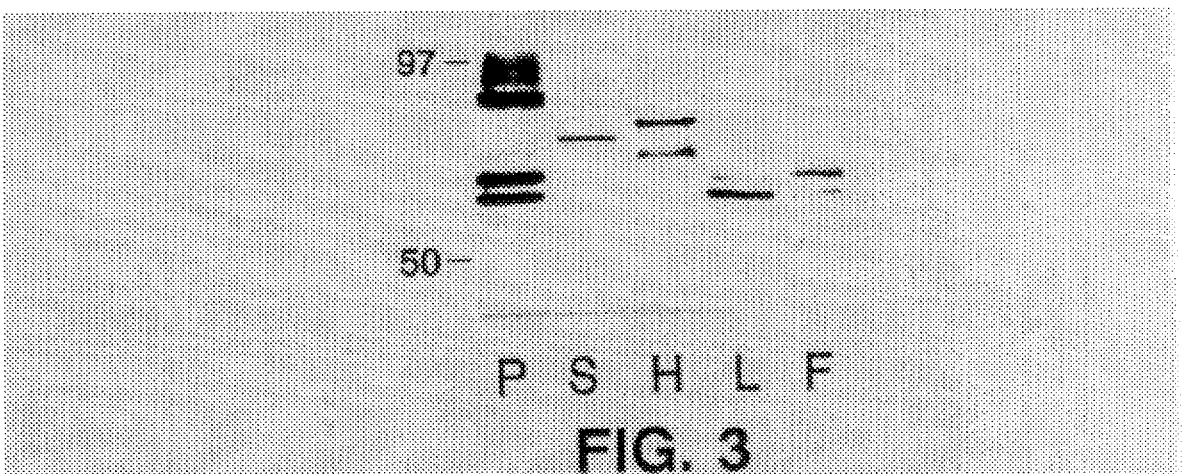
FIG. 3 shows a Western blot analysis of pooled cell lysates as described for FIG. 2 for individual Src family tyrosine kinase. Membranes used for antiphosphotyrosine immunoblots were stripped and reprobed with polyclonal anti-$p60^{c-src}$, $p58/64^{hck}$, $p53/56^{byn}$ or $p59^{c-fgr}$ antibodies. P, antiphosphotyrosine immunoblot of pooled lysates; S, stripped membrane reprobed with anti-$p60^{c-src}$ antibodies; H, stripped membrane reprobed with anti-$p58/64^{hck}$ antibodies; L, stripped membrane reprobed with anti-$p53/56^{byn}$ antibodies; F, stripped membrane reprobed with anti-$p59^{c-fgr}$ antibodies. Molecular size markers are in kilodaltons.

Antiphosphotyrosine immunoblot analysis of Triton X-100 soluble proteins of LPS-stimulated macrophages showed that major tyrosine phosphorylated proteins were in 55 to 90 KDa ranges (FIG. 2A). FIG. 3 shows a Western blot analysis of pooled cell lysates as described for FIG. 2 for individual Src family tyrosine kinase. Membranes used for antiphosphotyrosine immunoblots were stripped and reprobed with polyclonal anti-$p60^{c-src}$, $p58/64^{hck}$, $p53/56^{lyn}$ or $p59^{c-fgr}$ antibodies. P, antiphosphotyrosine immunoblot of pooled lysates; S, stripped membrane reprobed with anti-$p60^{c-src}$ antibodies; H, stripped membrane reprobed with anti-$p58/64^{hck}$ antibodies; L, stripped membrane reprobed with anti-$p53/56^{lyn}$ antibodies; F, stripped membrane reprobed with anti-$p59^{c-fgr}$ antibodies. Molecular size markers are in kilodaltons.

When antibodies in antiphosphotyrosine immunoblot membranes were stripped off and the membranes were reprobed with anti-Src family kinase antibodies (Santa Cruz), $p60^{c-src}$, $p58/64^{hck}$ and $p59^{c-fgr}$ were detected in the cell lysates (FIG. 3). Doublet bands for $p53/56^{lyn}$ (FIG. 2C) detected by immunoblot with anti-$p53/56^{lyn}$ antibodies were superimposed with the two major tyrosine phosphorylated bands in antiphosphotyrosine immunoblot of cell lysates as indicated by an arrow in FIGS. 2A and C.

Figure 4:
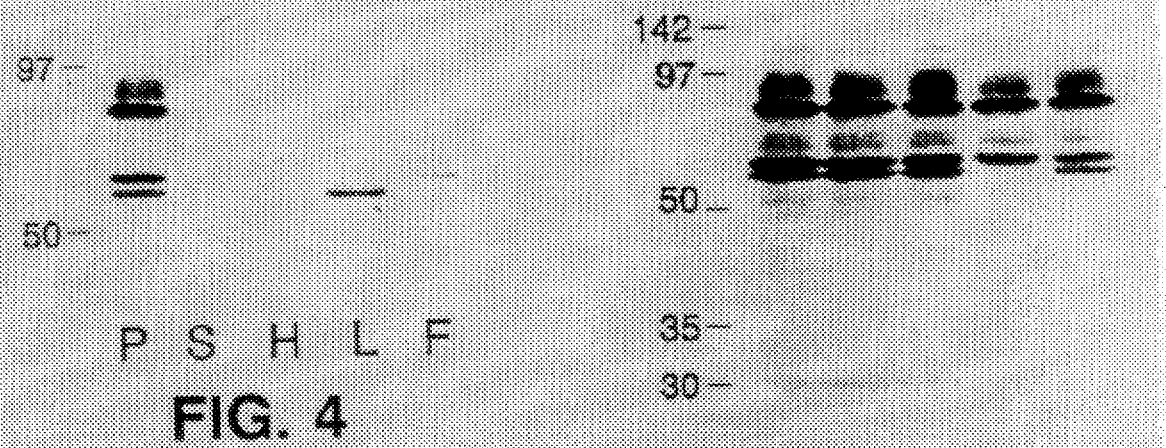
FIG. 4 shows an immunoblot analysis of Src tyrosine kinase immunoprecipitated from pooled cell lysates as in FIG. 2. P, antiphosphotyrosine immunoblot of pooled lysates; S, stripped membrane reprobed with anti-$p60^{c-src}$ antibodies; H, stripped membrane reprobed with anti-$p58/64^{hck}$ antibodies; L, stripped membrane reprobed with anti-$p53/56^{byn}$ antibodies; F, stripped membrane reprobed with anti-$p59^{c-fgr}$ antibodies. Molecular size markers are in kilodaltons.

Antiphosphotyrosine immunoblot of immunoprecipitates of cell lysates indicated that the $p53/56^{lyn}$ and $p59^{c-fgr}$ were the major tyrosine phosphorylated Src family tyrosine kinases (FIG. 4). FIG. 4 shows an antiphosphotyrosine immunoblot analysis of Src tyrosine kinase immunoprecipitated from pooled cell lysates as in FIG. 2. P, antiphosphotyrosine immunoblot of pooled lysates; S, stripped membrane reprobed with anti-$p60^{c-src}$ antibodies; H, stripped membrane reprobed with anti-$p58/64^{hck}$ antibodies; L, stripped membrane reprobed with anti-$p53/56^{lyn}$ antibodies; F, stripped membrane reprobed with anti-$p59^{c-fgr}$ antibodies. Molecular size markers are in kilodaltons.

Figure 5:
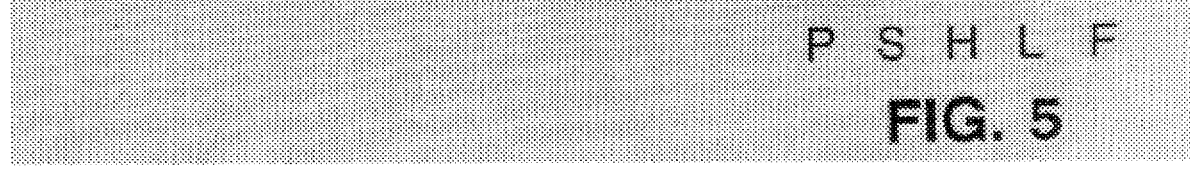
FIG. 5 shows an immunoblot analysis of cell lysates after immunoprecipitating individually Src family tyrosine kinase as in FIG. 4. P, antiphosphotyrosine immunoblot of pooled lysates without immunoprecipitation; S, cell lysate after depleting $p60^{c-src}$ by immunoprecipitation; H, cell lysate after depleting $p58/64^{hck}$ by immunoprecipitation; L, cell lysate after depleting $p53/56^{byn}$ by immunoprecipitation; cell lysate after depleting $p59^{c-fgr}$ by immunoprecipitation. Molecular size markers are in kilodaltons.

When the cell lysates after the immunoprecipitation were analyzed by antiphosphotyrosine immunoblot, the lower band superimposing with $p53/56^{lyn}$ disappeared completely in the sample for which $p53/56^{lyn}$ was removed by immunoprecipitation with anti-$p53/56^{lyn}$ antibodies (FIG. 5). FIG. 5 shows an antiphosphotyrosine immunoblot analysis of cell lysates after immunoprecipitating individually Src family tyrosine kinase as in FIG. 4. P, antiphosphotyrosine immunoblot of pooled lysates without immunoprecipitation; S, cell lysate after depleting $p60^{c-src}$ by immunoprecipitation; H, cell lysate after depleting $p58/64^{hck}$ by immunoprecipitation; L, cell lysate after depleting $p53/56^{lyn}$ by immunoprecipitation; cell lysate after depleting $p59^{c-fgr}$ by immunoprecipitation. Molecular size markers are in kilodaltons.

FIG. 6 shows a dose response by radicicol in inhibiting protein tyrosine kinase in LPS-stimulated macrophages. Inhibitory effects of radicicol and herbimycin A on tyrosine specific protein phosphorylation in LPS-stimulated macrophages were determined by antiphosphotyrosine immunoblotting as described in EXAMPLE 1. FIG. 6A shows an immunoblot after cells were pretreated with radicicol or herbimycin A at the indicated concentrations for 4 hours, and then stimulated with LPS (10 µg/ml) containing radicicol or herbimycin A. The control was pretreated with vehicle, DMSO (5 µl/ml) only. An arrow on the right indicates tyrosine phosphorylated protein bands superimposed with $p53/56^{lyn}$ bands shown below. Rad, radicicol; Herb, herbimycin A. Molecular size markers are shown in kilodaltons. FIG. 6B shows a Western blot analysis of $p53/56^{lyn}$ in the same samples used in FIG. 6A as described in FIG. 2C. LYN, $p53/56^{lyn}$.

Pretreatment of macrophages with radicicol in these studies resulted in suppression of levels of tyrosine phosphorylated proteins in time dependent and dose dependent fashions (FIGS. 2A and 6A). Pretreatment of macrophages with radicicol or herbimycin A resulted in significant reduction levels of $p53/56^{lyn}$ (FIG. 6B). This reduction in levels of $p53/56^{lyn}$ was correlated to suppressed levels of tyrosine phosphorylated proteins by radicicol or herbimycin A both in the time course (FIG. 2A) and the dose response studies (FIG. 6A). Pretreatment of macrophages with radicicol not only suppressed the basal levels (zero time) of tyrosine phosphorylated proteins, but also attenuated the stimulatory effect of LPS on protein tyrosine phosphorylation (FIG. 2A).

Figure 7:
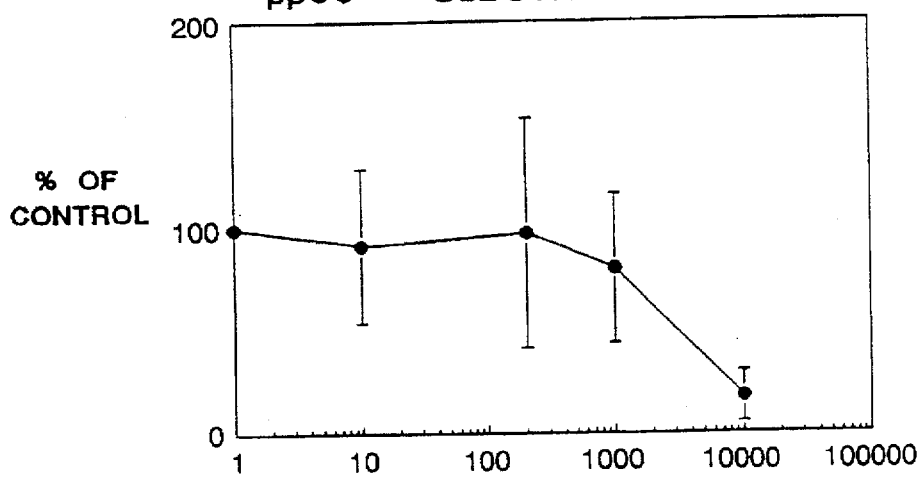
FIG. 7 shows the results of an in vitro kinase assay using purified p60$^{c-src}$, p60$^{c-src}$ kinase substrate peptide and $^{32}$P-ATP. Values are mean±SEM of three samples.

In vitro kinase assay using purified $p60^{c-src}$ kinase (UBI) and $p60^{c-src}$ kinase substrate peptide revealed that radicicol inhibits the kinase activity at much higher concentrations $IC_{50}=8.2$ µM, FIG. 7) than those required to suppress protein tyrosine phosphorylation in LPS-stimulated macrophages (FIG. 6A). FIG. 7 shows the results of an in vitro kinase assay using purified $p60^{c-src}$, $p60^{c-src}$ kinase substrate peptide and $^{32}$P-ATP. Values are mean±SEM of three samples.

Figure 10:
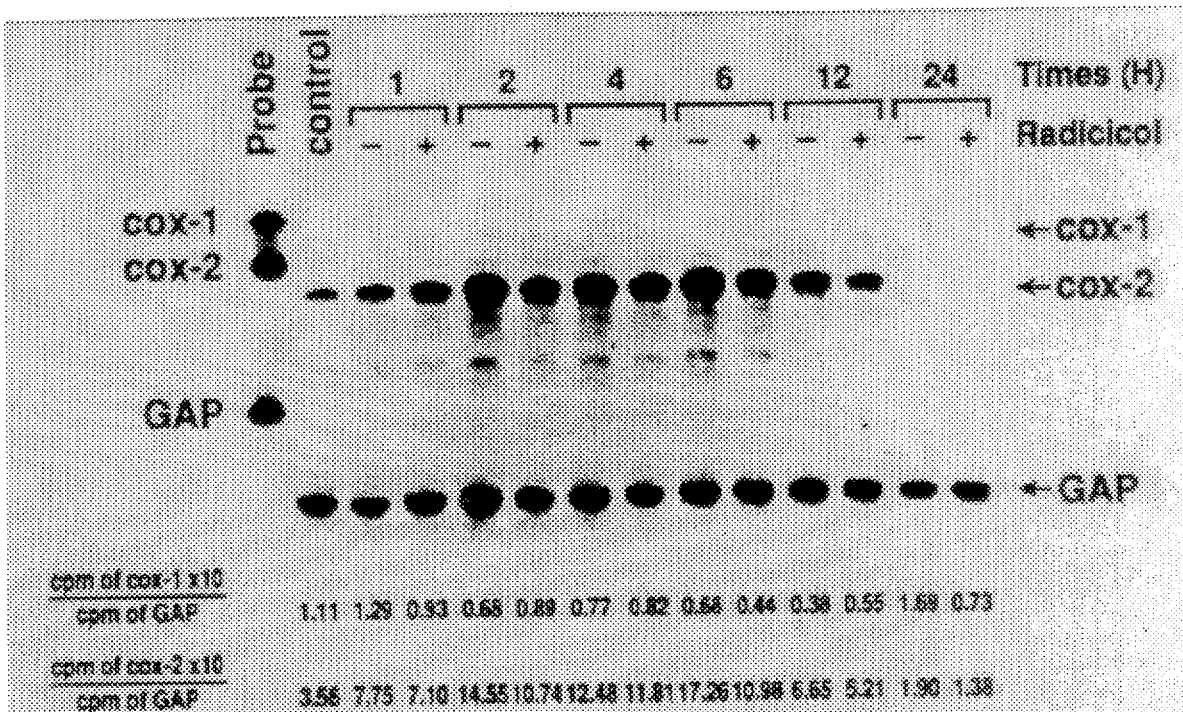
FIG. 10 shows a time course for levels of mRNA for COX-1, COX-2 and glyceraldehyde-3-phosphate dehydrogenase (GAP) in LPS-treated macrophages in the presence or absence of radicicol. The [γ-$^{32}$P] UTP-labeled COX-1, COX-2 and GAP were protected with the complementary mRNA from macrophages. The gel was scanned (AMBIS), and the radioactivities of COX-1 and COX-2 bands were factored relative to that of the GAP band.

The time course of protein tyrosine phosphorylation in LPS-stimulated macrophages shown in FIG. 2A was somewhat different from those reported with human monocytes and RAW 264.7 (Abelson virus-transformed murine macrophage cell line) stimulated with LPS. The maximum tyrosine phosphorylation occurred in 15 minutes and 30 minutes in RAW 264.7 cell and human monocytes, respectively (Stefanova, et al., *J. Biol. Chem.*, 268:20725–20728, 1993; Weinstein, et al., *Proc. Natl. Acad. Sci. USA*, 88:4148–4152, 1991). The maximum tyrosine phosphorylation in LPS-stimulated rat alveolar macrophages occurred much earlier than the maximum induction of COX-2 activity and protein (FIGS. 7 and 8A) or COX-2 mRNA (FIG. 10).

It has been demonstrated that LPS induces rapid tyrosine phosphorylation of isoforms of mitogen activated protein kinases (MAPK) in elicited murine peritoneal exudate macrophages and RAW 264.7 cells (Weinstein, et al., supra). Radicicol also inhibited tyrosine phosphorylation of MAPKs in a dose dependent fashion as shown in FIG. 2D. These inhibitory doses of radicicol were similar to those required to suppress the expression of COX-2 protein shown in FIG. 15. Some Src family tyrosine kinases, in association with cell surface proteins, participate in normal signalling pathways in hemopoietic cells including monocytes and macrophages (Bolen, et al., *FASEB J.* 3403–3409, 1992). It has been demonstrated that initial interaction of LPS with monocytes and macrophages involves a LPS-binding protein that binds to LPS and a glycosylphosphatidylinositol-anchored cell-surface, glycoprotein, CD14 (Han, et al., *J. Biol. Chem.*, 268:25009–25014, 1993) It was also shown that $p53/56^{lyn}$ was co-immunoprecipitated with CD14 in human monocytes (Stefanova, et al., supra). This suggested a critical role of Src family tyrosine kinases in the LPS/CD14-mediated signal transduction pathway in monocytes and macrophages.

The results shown in FIGS. 3–5 indicate that Src family tyrosine kinases are the major tyrosine-phosphorylated proteins, and that $p53/56^{lyn}$ is one of the major tyrosine-phosphorylated Src family tyrosine kinases in rat alveolar macrophages. These results are consistent with the results showing that $p53/56^{lyn}$ is the major Src family tyrosine kinase which is associated with CD14 in human monocytes (Stefanova, et al., supra).

Furthermore, radicicol inhibited tyrosine phosphorylation and levels of $p53/56^{lyn}$ in a time dependent and dose dependent fashion (FIGS. 2A, 2B, 6A and 6B). Inhibitory effects of radicicol on protein tyrosine phosphorylation required pretreatment of cells with radicicol for 4 hours prior to LPS stimulation. Such pretreatment of cells was also required for herbimycin A (Weinstein, et al., supra; Han, et al., supra).

The in vitro kinase assay showed that concentrations of radicicol required to inhibit the p60$^{c\text{-}src}$ kinase activity were much higher than those required to suppress protein tyrosine phosphorylation (FIG. 6A) or those required to suppress expression of COX-2 (FIG. 9). Similarly, concentrations of herbimycin A needed to suppress COX-2 expression and protein tyrosine phosphorylation in LPS-stimulated macrophages were much lower than those known to be required to inhibit p60$^{v\text{-}src}$ kinase activity in vitro. The IC$_{50}$ value of herbimycin A for the in vitro kinase activity was reported as 12 µM (Uehara, et al., *Biochem. Biophys. Res. Commun.*, 163:803–809, 1989).

Together, these results suggest that radicicol suppresses tyrosine phosphorylation of Src family tyrosine kinases in LPS-stimulated macrophages both by decreasing levels of enzyme proteins and inhibiting the enzyme activity. It has been shown that herbimycin A increased the degradation of p60$^{v\text{-}src}$ (Uehara, et al., *Cancer Res.*, 49:780–785, 1989). The mechanism by which radicicol inhibits protein tyrosine kinases is not known. It has been speculated that herbimycin A inactivates p60$^{v\text{-}src}$ kinase by irreversibly binding to SH group(s) of p60$^{v\text{-}src}$. The speculation was based on the fact that herbimycin A is readily inactivated by sulfhydryl compounds. These compounds abolished the inhibitory effect of herbimycin A on p60$^{v\text{-}src}$ kinase activity. It was postulated that his inactivation occurs through conjugation between highly polarized double bonds in the benzoquinone moiety of herbimycin A and the SH group of sulfhydryl compounds or Src kinases. Similarly, conjugation of SH group can occur at C-9 with a conjugated double bond or at C-5 and C-6 bearing an epoxide in the radicicol molecule as shown in FIG. 1. It was observed that dithiothreitol abolished the ability of radicicol to block p60$^{v\text{-}src}$ kinase activity (Kwon, et al., *Cancer Res.*, 52:6926–6930, 1992). However, them is no evidence as to whether sulfhydryl compounds also abolish effects of radicicol propagated to steps downstream of Src tyrosine kinases.

EXAMPLE 3

INHIBITION OF THE RECOVERY OF CYCLOOXYGENASE ENZYME ACTIVITY BY RADICICOL IN MACROPHAGES PRETREATED WITH ASPIRIN

Pretreatment of macrophages with aspirin (500 µM) for 2.5 hours resulted in inactivation of endogenous COX activity by more than 90%. In the previous study using the same cell type, it was shown that increased COX activity in LPS-stimulated macrophages which were pretreated with aspirin, results from selective expression of COX-2 (Lee, et al., supra). Therefore, de novo synthesized COX-2 in aspirin-pretreated macrophages can be accurately and conveniently quantitated by measuring recovered COX activity.

Figure 8:
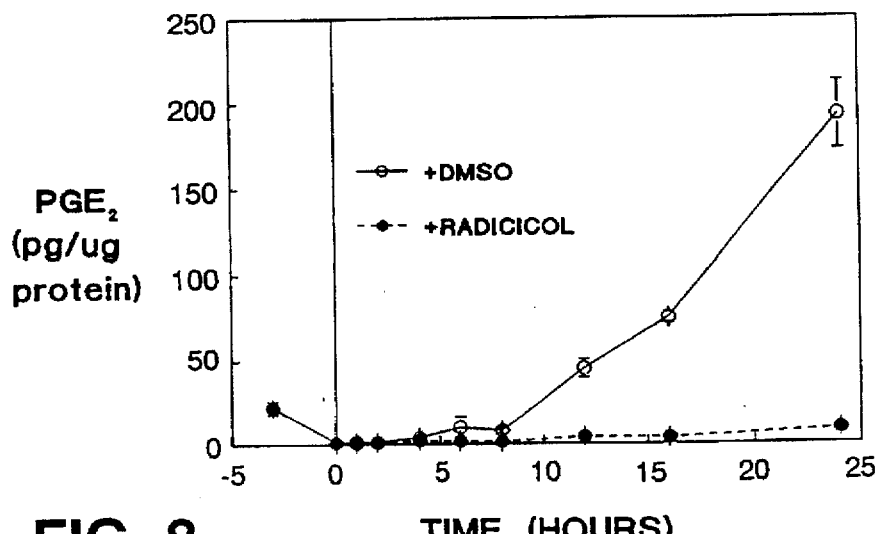
FIG. 8 shows a time course for the expression of COX activity induced by LPS and its inhibition by radicicol in macrophages pretreated with aspirin. Values for each time point are the mean of three samples.

The recovery of COX activity in aspirin pretreated and LPS-stimulated macrophaphages started only after 6 hours of incubation (FIG. 8). FIG. 8 shows a time course for the expression of COX activity induced by LPS and its inhibition by radicicol in macrophages pretreated with aspirin. Rat alveolar macrophages were allowed to attach for 2.5 hours in the presence of aspirin (500 µM) to inactivate endogenous cyclooxygenase, washed three times, and then incubated in RPMI with LPS (10 µg/ml) in the presence or absence of radicicol (200 ng/ml). After removing the media, cells were incubated with arachidonic acid (30 µM) for 10 minutes. The levels of PGE$_2$ produced from exogenous arachidonic acid were measured by radioimmunoassay to determine the activity of de novo synthesized cyclooxygenase. The value for 2.5 hours indicates the endogenous COX activity prior to aspirin treatment. Values for each time point are the mean of three samples.

This time course paralleled the time course of de novo synthesized COX-2 protein (Lee, et al., supra). Recovered COX activity after 16 hours of incubation was always greater than COX activity of unstimulated cells prior to aspirin treatment, although the magnitude of the difference varies with batches of cells. This indicates that the activity of COX-2 expressed as a result of LPS stimulation is much greater than that of COX-1 present in unstimulated cells. This suggests that COX-2 but not COX-1 plays a major role in producing prostanoids in response to inflammatory stimuli in macrophages. The inhibition of COX-2 expression by radicicol was not reversed during the 24 hour incubation period.

Figure 11:
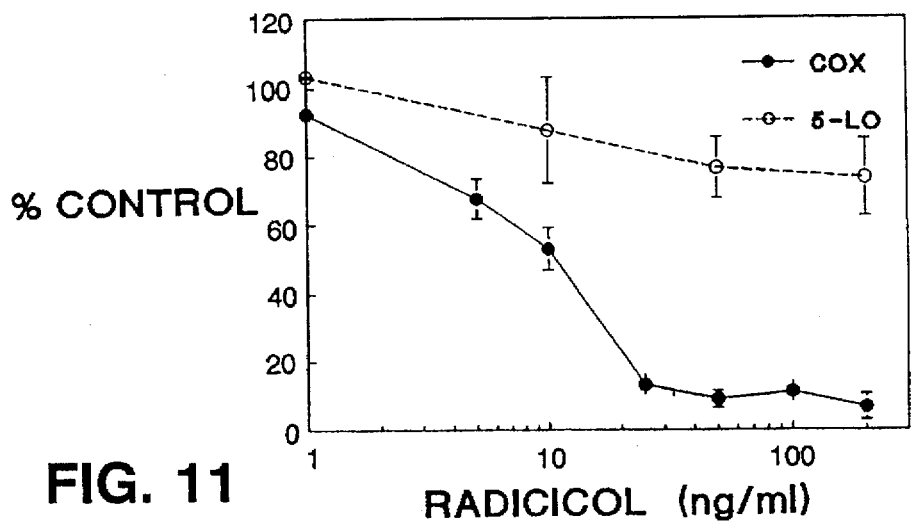
FIG. 11 shows the dose response by radicicol in inhibiting the recovery of COX activity and 5-lipoxygenase (5-LO) activity in LPS-stimulated macrophages. Rat alveolar macrophages pretreated with aspirin as described in the legend for FIG. 2 were incubated in RPMI with LPS and various concentrations of radicicol for 16 hours. The activity of 5-LO was determined by measuring the levels of 5-hydroxyeicosatetraenoic acid by radioimmunoassay. Values for each dose are the means of three to six samples.

The dose response to radicicol in inhibiting the recovery of COX activity showed that the IC$_{50}$ is 10 ng/ml (27 nM) as shown in FIG. 11. FIG. 11 shows the dose response by radicicol in inhibiting the recovery of COX activity and 5-lipoxygenase (5-LO) activity in LPS-stimulated macrophages. Rat alveolar macrophages pretreated with aspirin as described for FIG. 2 were incubated in RPMI with LPS and various concentrations of radicicol for 16 hours. The activity of de novo synthesized COX was determined by measuring the levels of PGE$_2$ produced from exogenous arachidonic acid as described for FIG. 8. The activity of 5-LO was determined by measuring the levels of 5-hydroxyeicosatetraenoic acid by radioimmunoassay. Values for each dose are the means of three to six samples.

These doses of radicicol did not significantly affect 5-lipoxygenase activity as determined by measuring 5-hydroxyeicosatetraenoic acid (5-HETE) produced from exogenous arachidonic acid (30 µM). Radicicol suppressed the expression of COX-2 protein but not COX-1 and glyceraldehyde-3-phosphate dehydrogenase (GAP) proteins. The rate of COX-2 protein synthesis, as determined by the immunoprecipitation assay using the specific COX-2 antibodies (Lee, et al., supra), showed a parallel dose-dependent inhibition by radicicol in macrophages which were metabolically labeled with [$^{35}$S] methionine in presence of LPS (FIG. 9A).

FIG. 9 shows the effects of radicicol on expressions of COX-2, COX-1 and glyceraldehyde-3-phosphate dehydrogenase (GAP). FIG. 9A shows, rat alveolar macrophages that were preincubated for 14 hours with LPS (10 µg/ml) and various concentrations of radicicol and then further incubated in methionine free RPMI containing 200 µCi of [$^{35}$S] methionine for 2 hours. Cells were lysed in the lysing buffer. Aliquots of the samples with equal amounts of radioactivity were precleared with the preimmune serum, immunoprecipitated with COX-2 antibodies, and subjected to SDS-polyacrylamide gel electrophoresis and fluorography as described in "EXAMPLE 1". FIG. 9B shows a Western blot analysis of rat alveolar macrophages incubated in RPMI with 3% serum for 16 hours with or without LPS and/or radicicol. For Western blot analysis, microsomes from lysed cells were used for COX-1 and whole lysate was used for GAP. Lane 1, cells incubated without LPS and radicicol; Lane 2, cells incubated with LPS (10 µg/ml) only; Lane 3, cells incubated with LPS and radicicol (50 ng/ml); Lane 4, cells incubated with LPS and radicicol (200 ng/ml).

When the same samples were precleared with COX-2 antiserum to remove COX-2 protein and then immunoprecipitated with COX antibodies which preferentially recognize COX-1 protein, no COX bands were detected in the autoradiograph. This result indicates that COX-1 is not synthesized in significant amounts during the two hour labeling period in LPS-treated macrophages.

Levels of COX-1 and GAP proteins were assessed by Western blot analysis (FIG. 9B). Levels of these enzymes in macrophages were not affected by either LPS or radicicol. Both COX-1 and GAP are products of housekeeping genes whose expression, normally is not stimulated by mitogens.

TABLE 1

$IC_{50}$ VALUES FOR RADICICOL INHIBITION OF COX-2

| CELL TYPE | MITOGEN | INCUBATION TIME (hr) | $IC_{50}$ (ng/ml) |
|---|---|---|---|
| Rat Al. Mac | LPS (10 µg/ml) | 16 | 10 |
| Rat Al. Mac | PMA (200 ng/ml) | 8 | NI |
| Rat SMC | IL-1 (1 ng/ml) | 8 | 400 |
| Rat SMC | LPS (10 µg/ml) | 12 | 100 |
| Human Monocytes | LPS (100 ng/ml) | 24 | 2 |

$IC_{50}$ was estimated by determining % inhibition at five different dose levels of radicicol.
NI-not inhibited by radicicol at concentrations up to 1 µg/ml. The incubation time for each cell type and mitogen was selected from respective time course in which the maximum induction of COX-2 activity occurred.
Al. Mac, alveolar macrophages; SMC, smooth muscle cells; IL-1, interleukin-1β; PMA, phorbol 12-myristate 13-acetate.

Radicicol also inhibited the LPS-induced expression of COX-2 in rat smooth muscle cells and human peripheral blood monocytes. Furthermore, radicicol inhibited the expression of COX-2 induced by IL-1β-induced COX-2 expression was much greater than that for the inhibition of COX-2 expression induced by LPS (Table 1).

Radicicol at concentrations up to 1000 ng/ml did not significantly affect the expression of COX-2 induced by phorbol 12-myristate 13-acetate (PMA) in rat alveolar macrophages (Table 1 ). It was also shown that another protein tyrosine kinase inhibitor, herbimycin A only weakly inhibits PMA-induced release of [$^3$H]-arachidonic acid metabolites in macrophage-like cell line (RAW 264.7), whereas it dramatically inhibits LPS-induced release of [$^3$H]-arachidonic acid metabolites (Weinstein, et al., supra). It has been demonstrated that PMA-stimulated c-raf activity in human T cells and some of functional effects of PMA were resistant to the inhibitory effects of herbimycin A (June, et al., Proc. Natl. Acad. Sci. USA, 87:7722–7726, 1990). These results suggest that protein tyrosine phosphorylation is proximal to protein kinase C activation in these signal transduction pathways.

It has been well documented that endotoxin LPS induces rapid protein tyrosine phosphorylation in macrophages (Stefanova, et al., supra; Weinstein, et al., supra; Han, et al., supra). In addition to radicicol, other tyrosine kinase inhibitors also suppressed LPS-induced expression of COX-2, although $IC_{50}$ values of these inhibitors were much greater than that of radicicol [22 µM, 52 nM and 357 µM for genistein, herbimycin A and tryphostin (AG-494), respectively]. Earlier, it was shown that PMA-induced expression of COX-2 was not inhibited by radicicol. Together, these results suggest that tyrosine protein phosphorylation is the proximal step in the LPS-induced signal transduction pathway leading to the induction of COX-2 expression in macrophages, and that the inhibitory effect of radicicol on LPS-induced COX-2 expression is due at least in part to the suppression of activities of tyrosine kinases.

EXAMPLE 4

SUPPRESSION OF STEADY STATE LEVELS OF COX-2 mRNA BY RADICICOL

The RNase protection assays with multiple probes were carried out to measure simultaneously the ratios of mRNA levels for COX-1 and COX-2 to those for GAP, as shown in FIG. 10. FIG. 10 shows a time course for levels of mRNA for COX-1, COX-2 and glyceraldehyde-3-phosphate dehydrogenase (GAP) in LPS-treated macrophages in the presence or absence of radicicol. Rat alveolar macrophages were incubated with LPS in the presence or absence of radicicol (100 ng/ml) for specified times. Total RNA was extracted and hybridized with riboprobes, as described in Example 1. The [γ-$^{32}$P] UTP-labeled COX-1, COX-2 and GAP were protected with the complementary mRNA from macrophages. The gel was scanned (AMBIS), and the radioactivities of COX-1 and COX-2 bands were factored relative to that of the GAP band.

Figure 12:
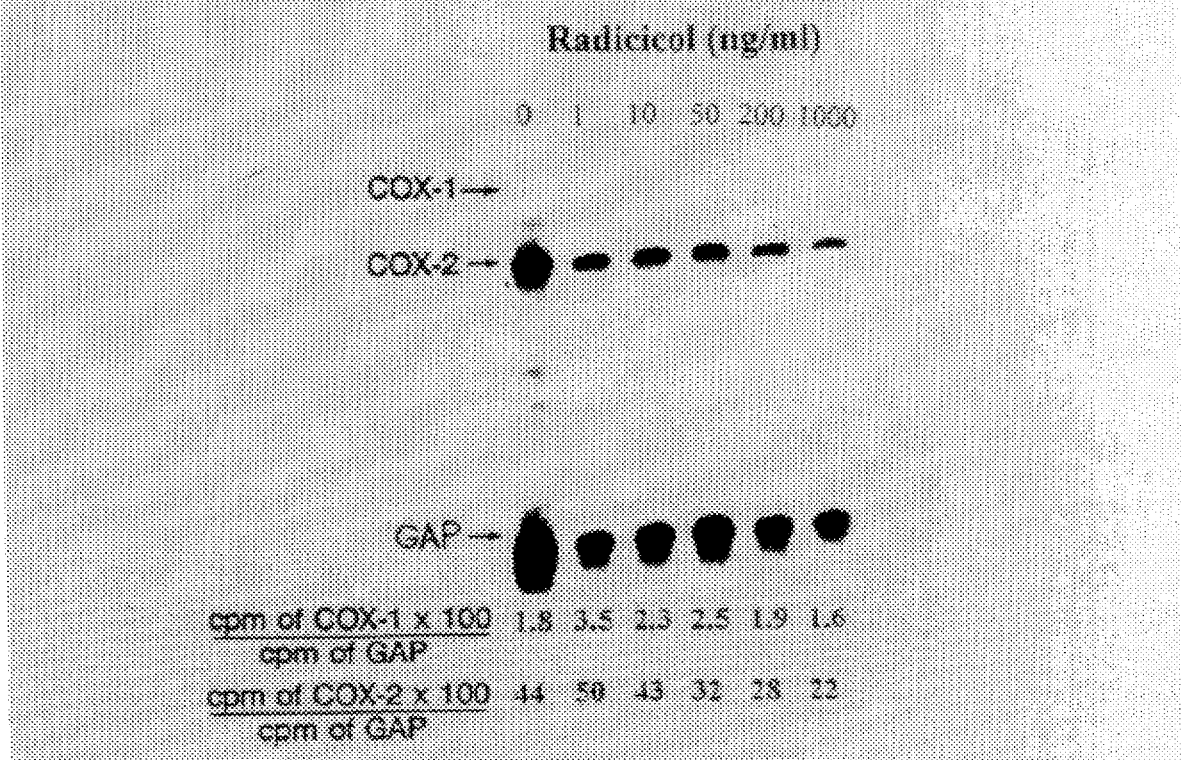
FIG. 12 shows a dose response of COX-1, COX-2 and GAP mRNA levels to radicicol. Rat alveolar macrophages were incubated with LPS in presence of various concentrations of radicicol for two hours. Levels of mRNA were determined by RNase protection assay.

The relative abundance of mRNA for COX-1 was much less than for COX-2. Radicicol did not appear to affect the steady state levels of mRNA for COX-1. Radicicol slightly inhibited mRNA levels for COX-2; only 50% inhibition was shown at 1000 ng/ml (FIG. 12). However, the maximum inhibition of the rate of synthesis of COX-2 protein by radicicol occurred at concentrations far below 200 ng/ml, as assessed by immunoprecipitation (FIG. 9A). FIG. 12 shows a dose response of COX-1, COX-2 and GAP mRNA levels to radicicol. Rat alveolar macrophages were incubated with LPS in presence of various concentrations of radicicol for two hours. Levels of mRNA were determined by RNase protection assay, as described for FIG. 10.

The maximum inhibition of the activity of de novo synthesized COX-2 by radicicol occurred below 30 ng/ml as shown in FIG. 11. The magnitude of the inhibition of COX-2 protein synthesis by radicicol was much greater than that of COX-2 mRNA.

Figure 13A:
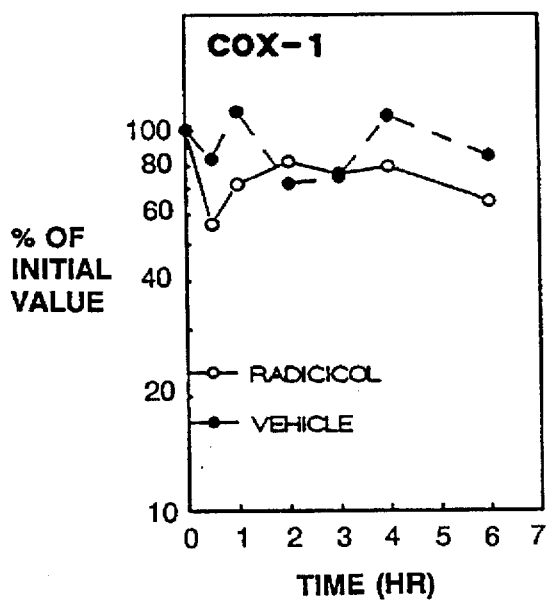
FIG. 13 shows the effect of radicicol on the stability of COX-1 and COX-2 mRNA. The effect of radicicol on COX-1 and COX-2 mRNA stability was examined by stimulating macrophages with LPS for 2 hours in the presence or absence of radicicol (100 ng/ml). Actinomycin D (Act D) at a final concentration of 2 µg/ml was added to block further transcription, and levels of COX-1 and COX-2 mRNA were monitored at specified time intervals over a period of 6 hours after the addition of Act D by RNase protection assay. GAP mRNA, which is known t have a long half-life, was used as an internal control for RNA loading. The radioactivity was quantitated by AMBIS. Percents of initial levels (cpm of COX-1 or COX-2×10÷cpm of GAP) were plotted against the incubation time after the addition of Act D. Panel A, COX-1 mRNA stability. Panel 13B, COX-2 mRNA stability.
Figure 13B:
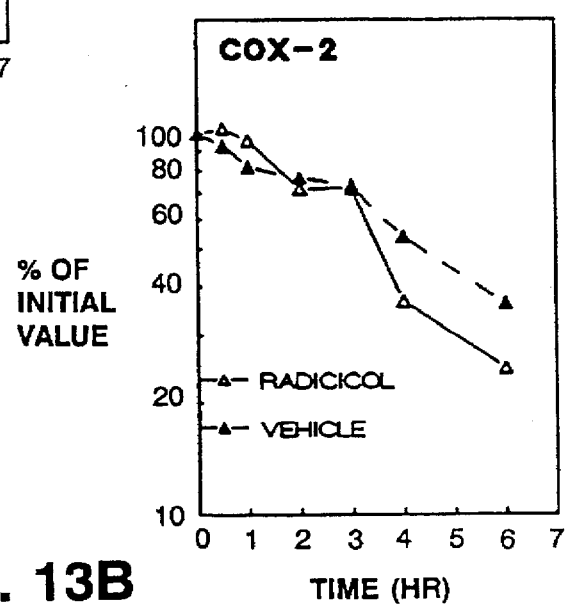
Figure 16A:
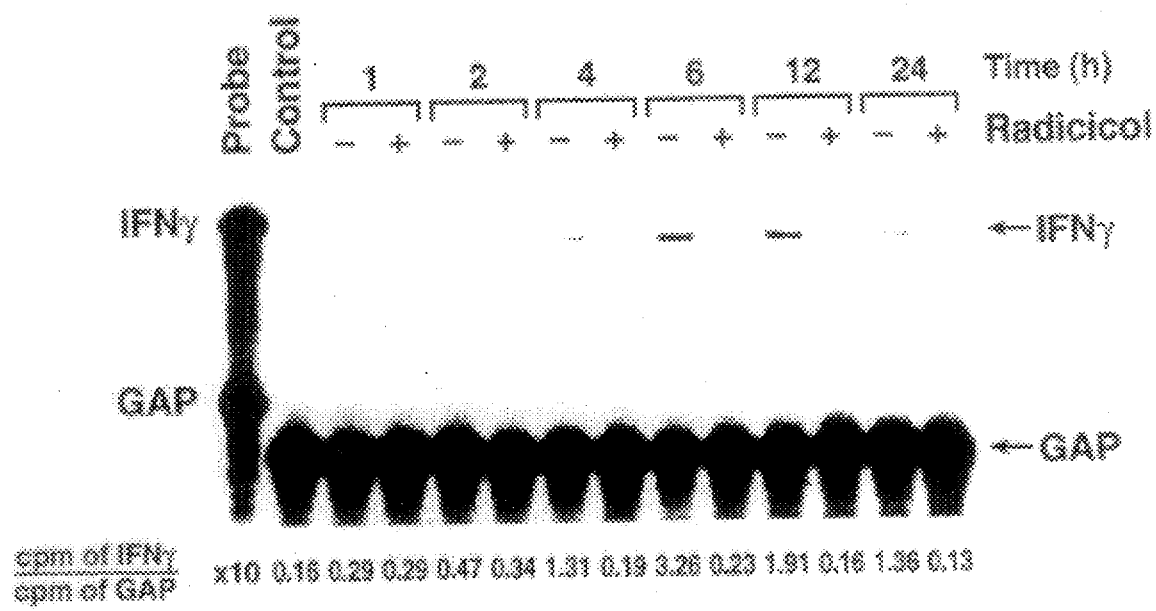
FIG. 16 is an RNase protection assay which shows a time course for levels of mRNA for IFNγ (A,B); MCP-1 (C,D); MIP-2, KC (E); PTPase (F); GM-CSF (G); TF, IL-6 (H); and IL-1α (I) in macrophages stimulated with LPS in the presence or absence of radicicol, as indicated. All figures include GAP as a control.
Figure 16B:
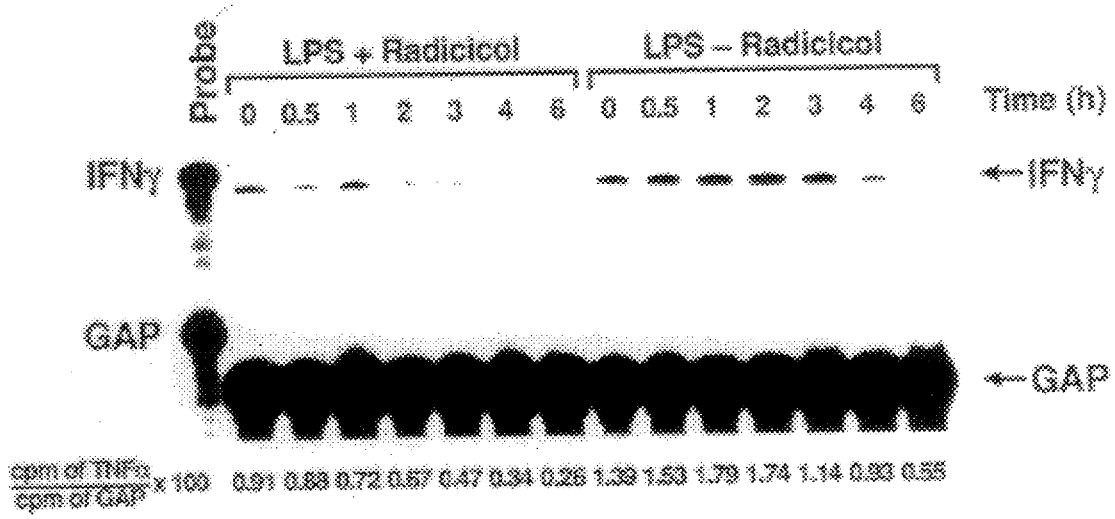
Figure 16C:
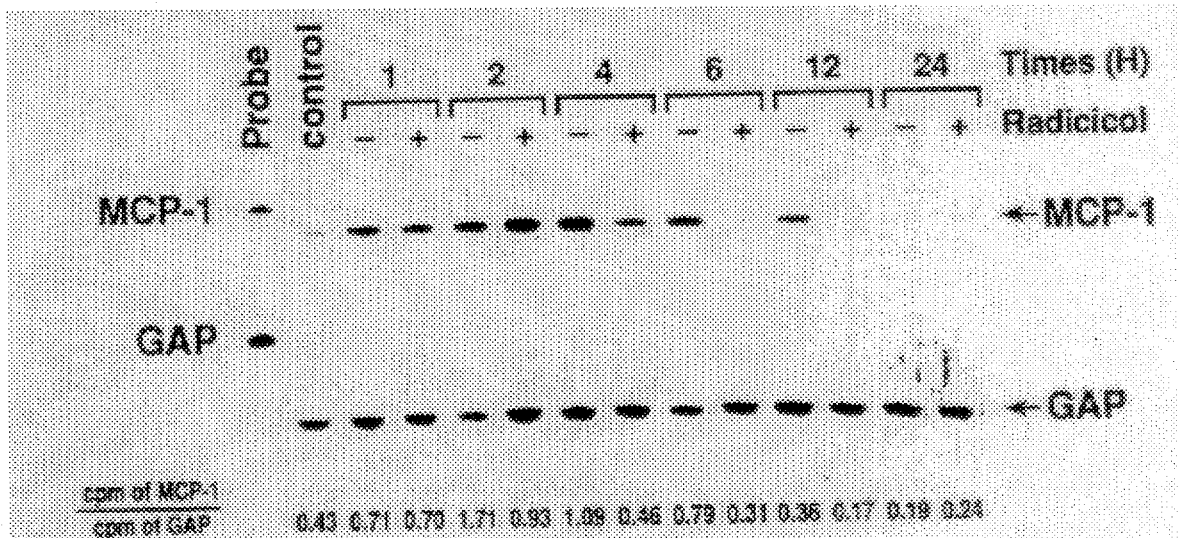
Figure 16D:
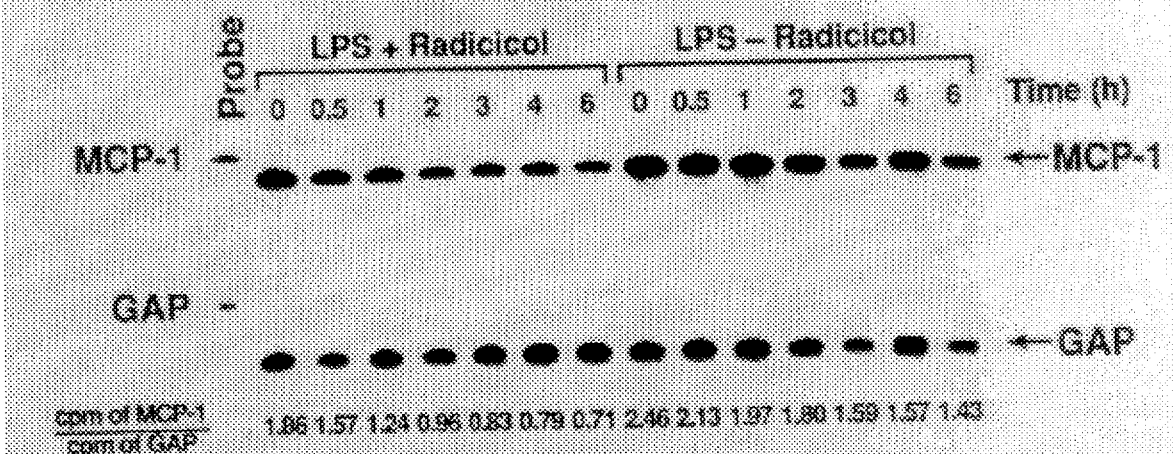
Figure 16E:
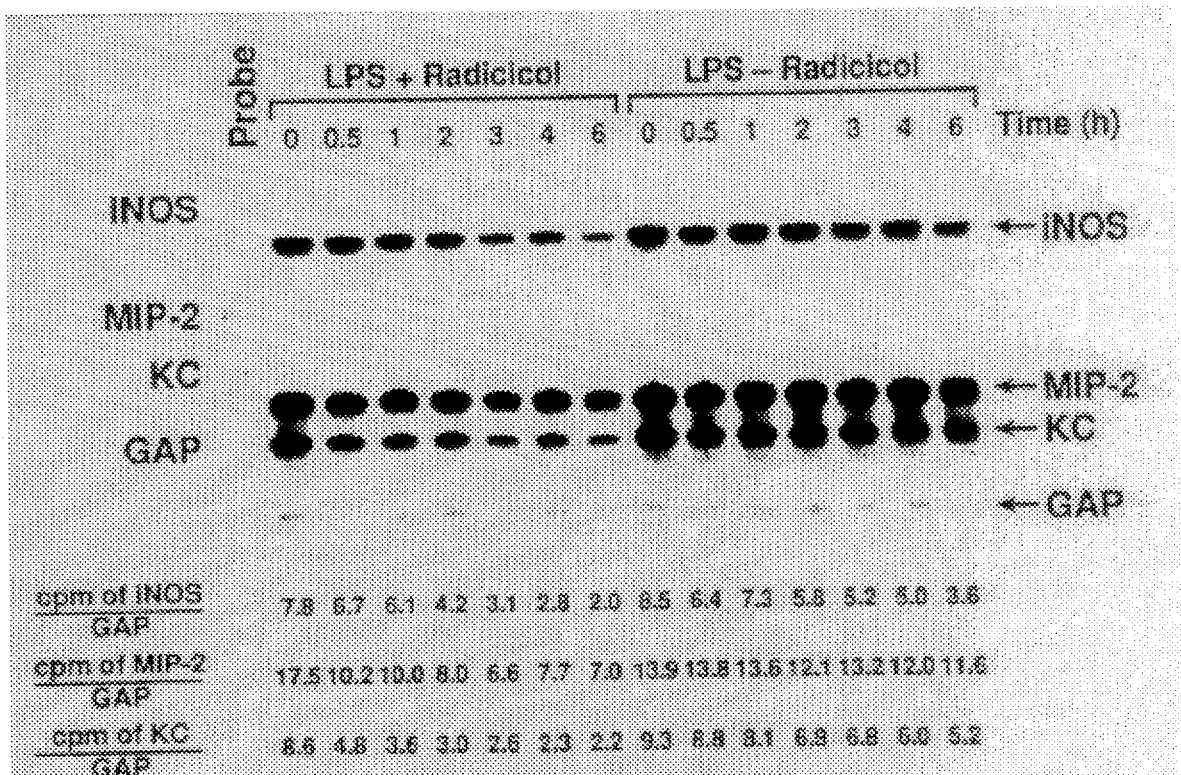
Figure 16F:
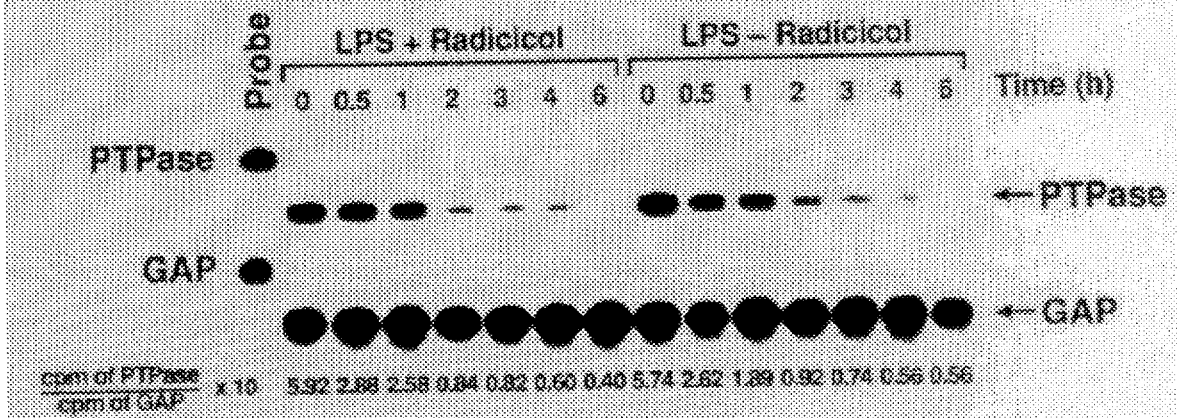
Figure 16G:
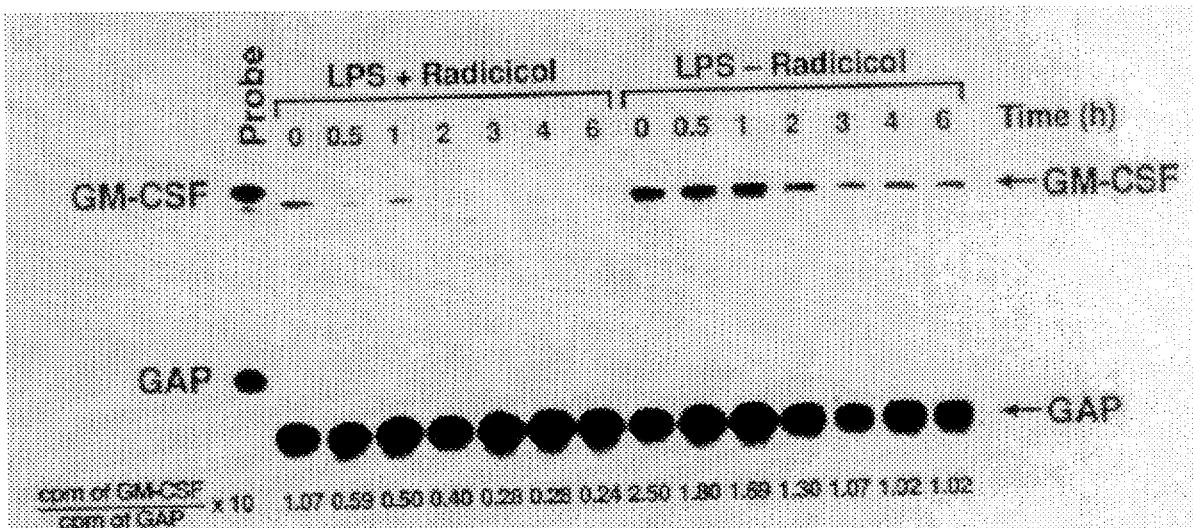
Figure 16H:
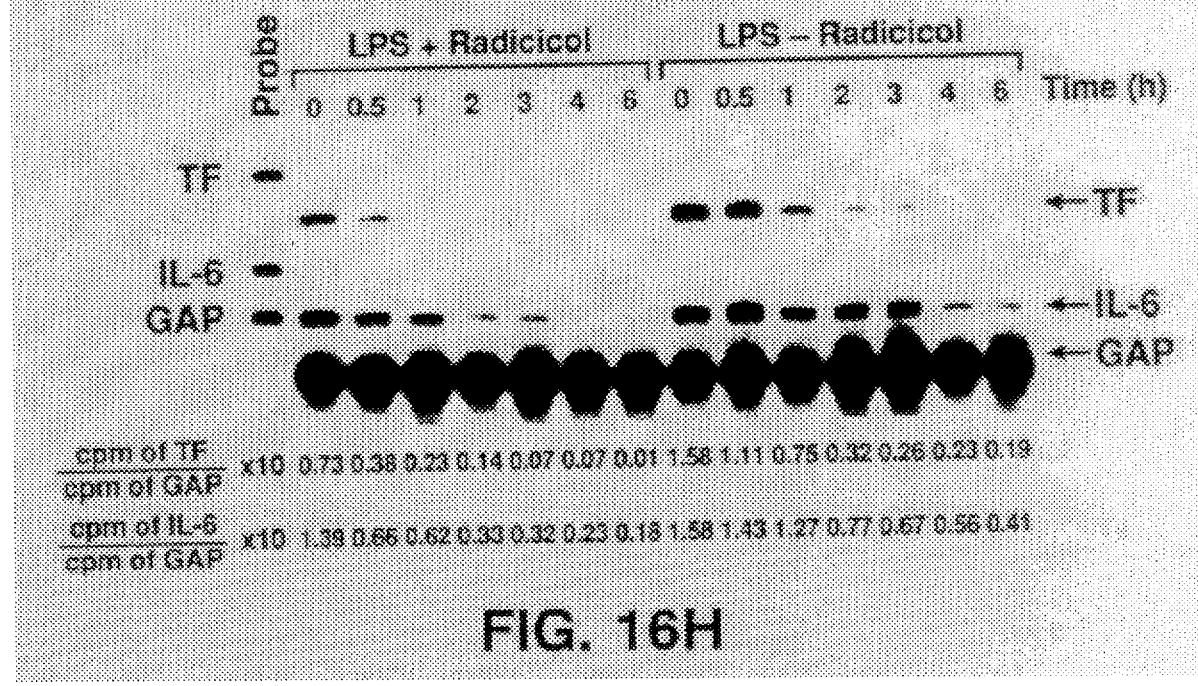
Figure 16I:
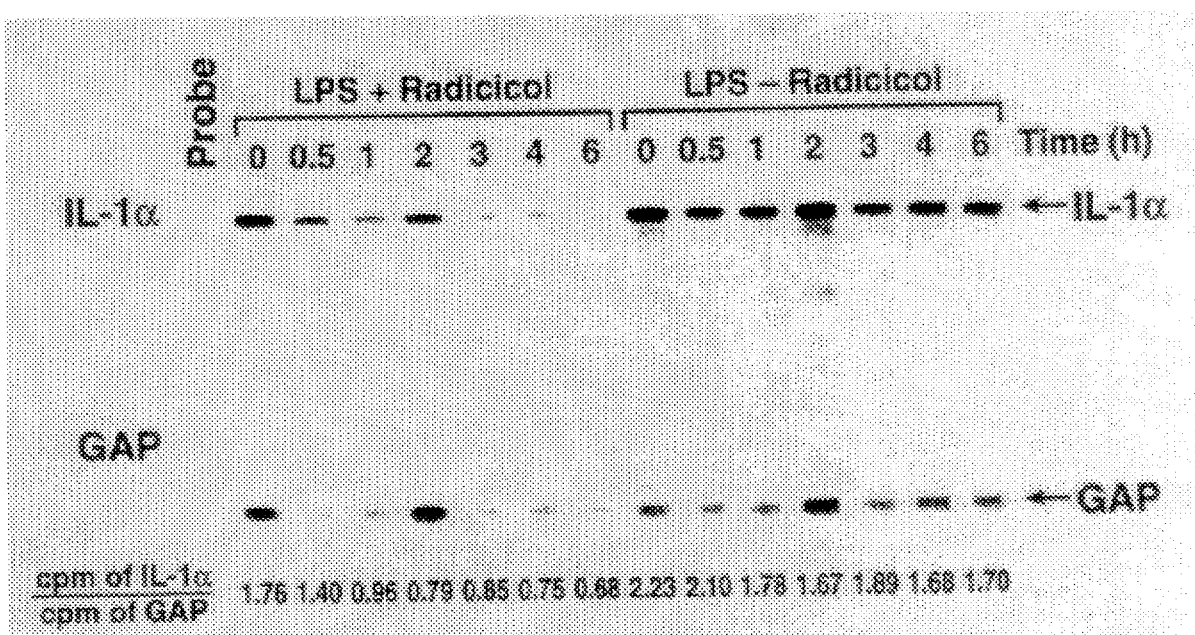

FIG. 13 shows the effect of radicicol on the stability of COX-1 and COX-2 mRNA. The effect of radicicol on COX-1 and COX-2 mRNA stability was examined by stimulating macrophages with LPS for 2 hours in the presence or absence of radicicol (100 ng/ml). Actinomycin D (Act D) at a final concentration of 2 µg/ml was added to block further transcription, and levels of COX-1 and COX-2 mRNA were monitored at specified time intervals over a period of 6 hours after the addition of Act D by RNase protection assay. GAP mRNA, which is known to have a long half-life, was used as an internal control for RNA loading. The radioactivity was quantitated by AMBIS as shown in FIG. 10. Percents of initial levels (cpm of COX-1 or COX-2×10+cpm of GAP) were plotted against the incubation time after the addition of Act D. Panel A shows COX-1 mRNA stability. Panel B shows COX-2 mRNA stability.

The rate of degradation of COX-2 mRNA was not significantly affected by radicicol (FIG. 13). The half-life of COX-2 mRNA was about four hours. The shorter half-life of COX-2 mRNA, as compared to that of COX-1 mRNA, is consistent with the presence of 14 copies of AUU motif conferring mRNA instability in the 3' untranslated region of rat COX-2 mRNA (Feng, et al., supra), These results suggest that radicicol inhibits COX-2 expression mainly at post-transcriptional steps.

EXAMPLE 5

RADICICOL DID NOT AFFECT THE ENZYME ACTIVITY OF EITHER COX-1 OR COX-2

The effect of radicicol on the enzyme activity of endogenous COX-1 was assessed by measuring COX activity in macrophages (which are not treated with aspirin or LPS) incubated with radicicol (100 ng/ml) for 1 hour. It was found in the previous studies (Lee, et al., supra) that resting unstimulated alveolar macrophages contain only COX-1 but not COX-2. The results showed that the level of PGE$_2$ produced from exogenous arachidonic acid (30 µM) in resting macrophages treated with radicicol was not different from that of cells treated with the vehicle: 35.9±3.7 and 33.2±4.2 pg/µg protein for radicicol treated cells and untreated cells, respectively. This result indicates that radicicol does not affect the enzyme activity of COX-1.

To determine the direct effect of radicicol on the enzyme activity of COX-2, macrophages were pretreated with aspirin (500 µM) for 4 hours to inactivate the endogenous COX, washed three times and then further incubated with LPS for 16 hours in order to maximally stimulate COX-2 expression. After removing the medium, cells were incubated with radicicol (100 ng/ml) or with the vehicle (dimethyl sulfoxide) for 1 hour and then COX activity was determined as described above. COX activity in these cells reflects specifically that of COX-2 because endogenous COX-1 was inactivated by aspirin and LPS induces selective expression of COX-2 in macrophages as shown in our previous study (Lee, et al., supra). The results showed that the level of PGE$_2$ produced from exogenous arachidonic acid in cells treated with radicicol was 150.2±9.3 (pg/µg protein, n=3), whereas that in cells treated with the vehicle was 121.1±8.8 (pg/µg protein, n=3). The enzyme activities of purified COX-1 and COX-2 were also not affected by radicicol (1000 ng/ml). COX-1 activities were 3.82±0.42 and 5.40±0.78 nmole/µg protein/10 minutes (n=4) for the vehicle and radicicol treated samples, respectively. These results indicate that radicicol does not directly affect the enzyme activities of COX-1 and COX-2 but it specifically suppresses the expression COX-2 in LPS-stimulated alveolar macrophages.

The protein tyrosine kinase inhibitor genistein has been shown to inhibit platelet-activating factor-stimulated PGE$_2$ production in LPS-primed p388D1 macrophage-like cells (Glaser, et al., *J. Biol. Chem.* 265:8658–8664, 1990). Genistein and another protein tyrosine kinase tyrphostin-25 inhibited PGE$_2$ production in murine resident peritoneal macrophages stimulated with zymosan, calcium ionophore A23187, and PMA (Glaser, et al., supra). It was shown that these inhibitors had no inhibitory effect on cyclooxygenase activity in the intact macrophages (Glaser, et al., *Biochemical Pharmacol.*, 45:711–721, 1993). Therefore, it was speculated that the inhibition of PGE$_2$ production by protein tyrosine kinase is resulting from reduced arachidonic acid release from membrane lipids by phospholipase A$_2$. The results showing that protein tyrosine kinase inhibitors suppress the expression of COX-2 suggest that the inhibition of PG production in LPS-stimulated macrophages by these inhibitors is due at least in part to the suppression of COX-2 expression.

EXAMPLE 6

INHIBITION OF EXPRESSION OF PROINFLAMMATORY AGENTS BY RADICICOL

The RNase protection assay with multiple probes were carried out to measure simultaneously the ratios of mRNA levels for IL-1 and TNF-α to those for GAP, as described in FIG. 10. FIG. 14 shows a time course for levels of mRNA for IL-1, TNF-α and glyceraldehyde-3-phosphate dehydrogenase (GAP) in LPS-treated macrophages in the presence or absence of radicicol (as described in FIG. 10). Rat alveolar macrophages were incubated with LPS in the presence or absence of radicicol (100 ng/ml) for specified times. Total RNA was extracted and hybridized with riboprobes, as described in Example 1. The [γ-$^{32}$P] UTP-labeled IL-1 and TNF-α and GAP were protected with the complementary mRNA from macrophages. The gel was scanned (AMBIS), and the radioactivities of IL-1 and TNF-α bands were factored relative to that of the GAP band. The results shown in FIGS. 14 and 15 indicate that radicicol effectively inhibited expression of IL-1 and TNF-α in LPS-stimulated macrophages.

FIG. 15 shows the effects of radicicol on expression of COX-2, COX-1, IL-1, TNF-α, and glyceraldehyde-3-phosphate dehydrogenase (GAP). FIG. 15A shows immunoprecipitated COX-2 protein in rat alveolar macrohages incubated with LPS (10 µg/ml) and various concentrations of radicicol and further incubated with 200 µCi [$^{35}$S]-methionine for 2 hours. Samples were immunoprecipitated with COX-2 antibodies and subjected to SDS-polyacrylamide gel electrophoresis and fluorography. At concentrations of between 10 and 1000 ng/ml, radicicol inhibited COX-2 expression.

FIG. 15B shows a Western blot analysis of lysates of rat alveolar macrophage incubated in RPMI with 3% serum for 16 hours with or without LPS and/or radicicol. Microsomes from lysed cells were used for COX-1 and whole lysate was used for GAP. Lane 1, cells incubated without LPS and radicicol; Lane 2, cells incubated with LPS (10 µg/ml) only; Lane 3, cells incubated with LPS and radicicol (50 ng/ml); Lane 4, cells incubated with LPS and radicicol (200 ng/ml). TNF-α and PGE2 were measured by radioimmunoassay of the supernatant.

A comparison of lanes 2–4 for IL-1 shows that radicicol at 50 ng/ml effectively reduces IL-1 expression, while radicicol treatment at 200 ng/ml almost completely abolishes IL-1 protein. Radicicol had little or no effect on COX-1 and GAPDH protein.

RNase protection assays on LPS stimulated macrophages in the presence or absence of radicicol were also performed as described above for FIGS. 10 and 14, utilizing various probes for other pro-inflammatory agents.

FIG. 16 shows the results of an Rnase protection assay time course for levels of mRNA. mRNA for many proinflammatory agents was reduced in LPS stimulated macrophages treated with radicicol. FIG. 16 shows IFNγ (A,B); MCP-1 (C,D); MIP-2, KC (E); PTPase (F); GM-CSF (G); TF, IL-6 (H); and IL-1 α (I) in macrophages stimulated with LPS in the presence or absence of radicicol, as indicated. All panels include GAP as a control.

FIG. 17 shows the effect of LPS in the presence or absence of radicicol on the stability of mRNA for the proinflammatory agents in FIG. 16. Stability of mRNA was measured, as in FIG. 13. The effect on TNF-α (A); iNOS (B); IL- 1α (C); MIP2 (D); IL-1β (E); KC (F); MCP-1 (G); TF (H); GM-CSF (I); IL-6 (J); and PTPase (K) mRNA stability is shown as a percentage as compared with GAP. (■, LPS+radicicol; ▲ LPS-radicicol). The results indicate that radicicol affects stability of mRNA for various cytokines and other genes such as IL-1β (E), MIP2 (D), KC (F), GM-CSF (I) and IL-6 (J). The rate of degradation for TF (H) and PTPase (K) was not significantly affected, suggesting that radicicol inhibits TF and PTPase expression mainly at post transcriptional steps.

EXAMPLE 7

IN VIVO SUPPRESSION OF COX-2 EXPRESSION BY RADICICOL IN RATS WITH EXPERIMENTAL GLOMERULONEPHRITIS (GN)

The ability of radicicol to suppress COX-2 expression in vivo was evaluated in rats with experimental GN induced by anti-GBM antibodies. It was shown in our previous study that the expression of COX-2 mRNA was dramatically increased in glomeruli of rats with the experimental GN (Feng, et al., supra). mRNA for COX-2 is not detected in glomeruli of healthy rats. Glomerular injuries in this animal disease model are dependent on infiltrating inflammatory cells such as neutrophils and macrophages.

Figure 18:
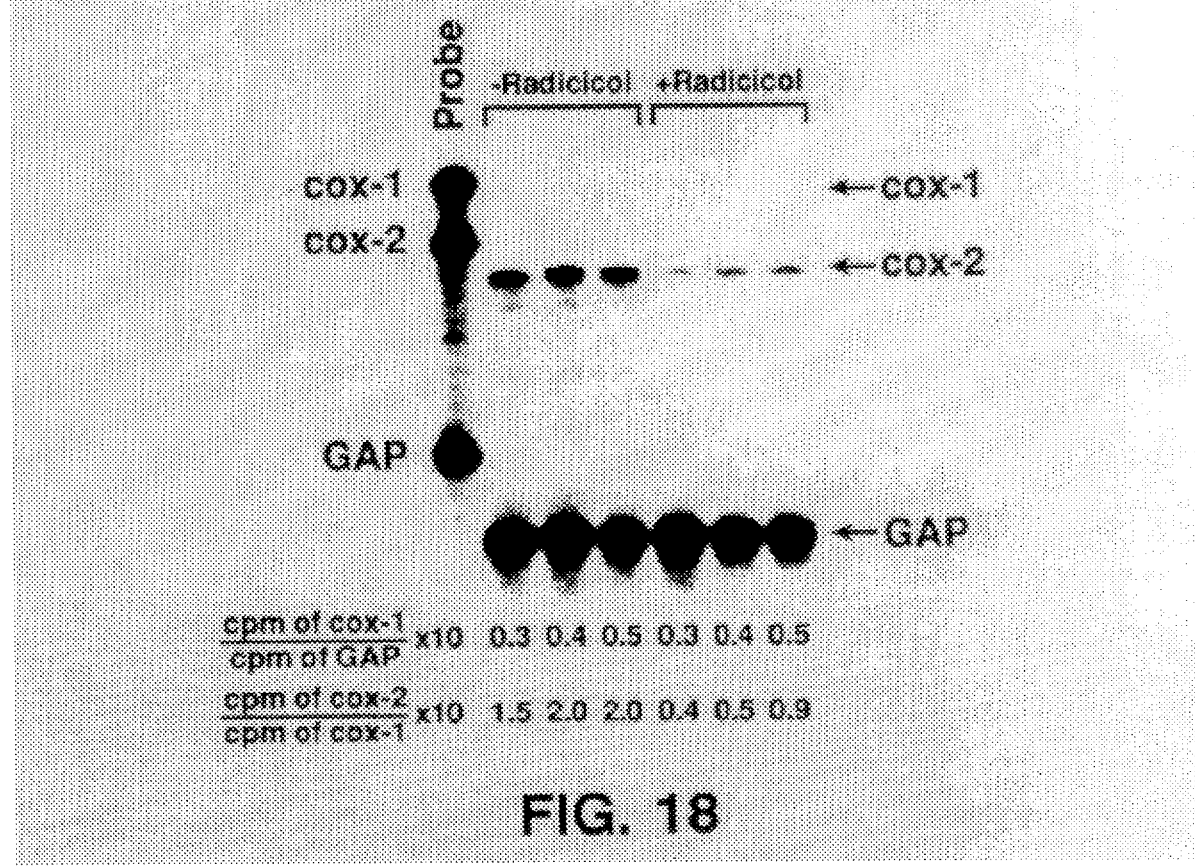
FIG. 18 shows in vivo effects of radicicol on expressions of COX-1, COX-2 and glyceraldehyde-3-phosphate dehydrogenase in rats with experimental glomemlonephritis. The rats were sacrificed after 4 hours and 24 hours following anti-GBM antibody injection.
Figure 17A:
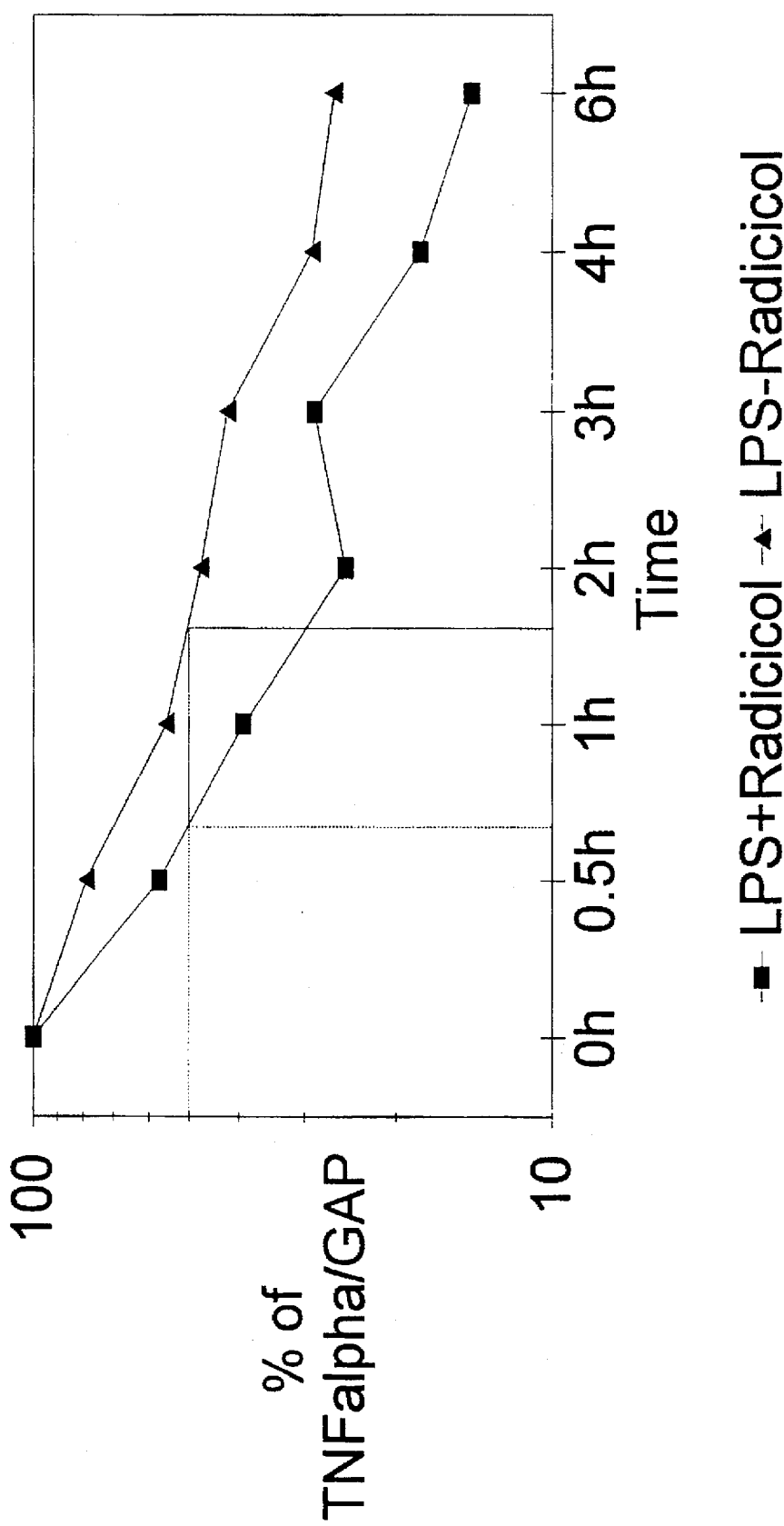
FIG. 17 shows the effect of LPS in the presence or absence of radicicol on the stability of mRNA, as in FIG. 13. The effect on TNF-α (A); iNOS (B); IL-1α (C); MIP2 (D); IL-1β (E); KC (F); MCP-1 (G); TF (H); GM-CSF (I); IL-6 (J); and PTPase (K) mRNA stability is shown as a percentage as compared with GAP. (■, LPS+radicicol; ▲ LPS-radicicol).
Figure 17B:
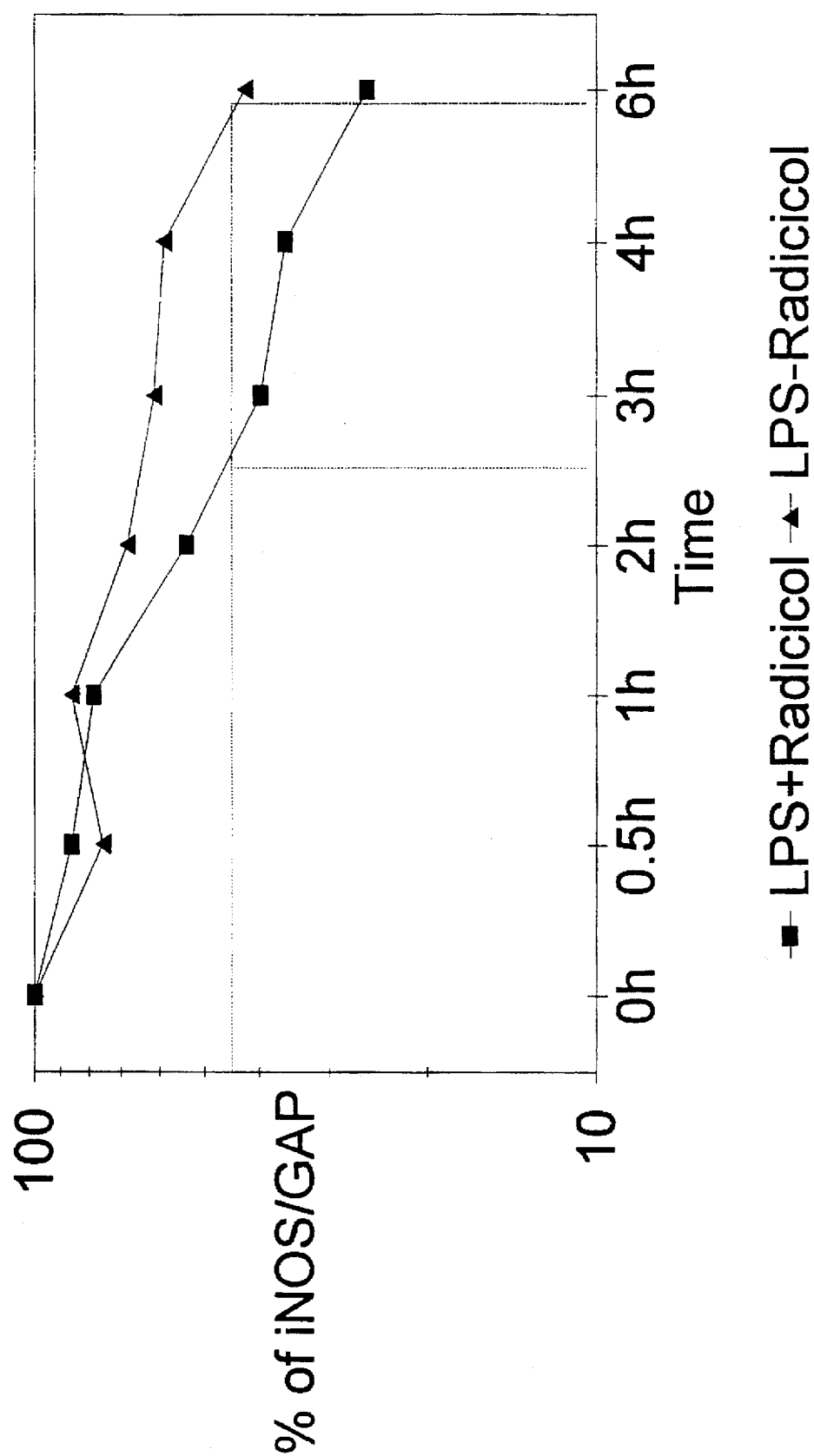
Figure 17C:
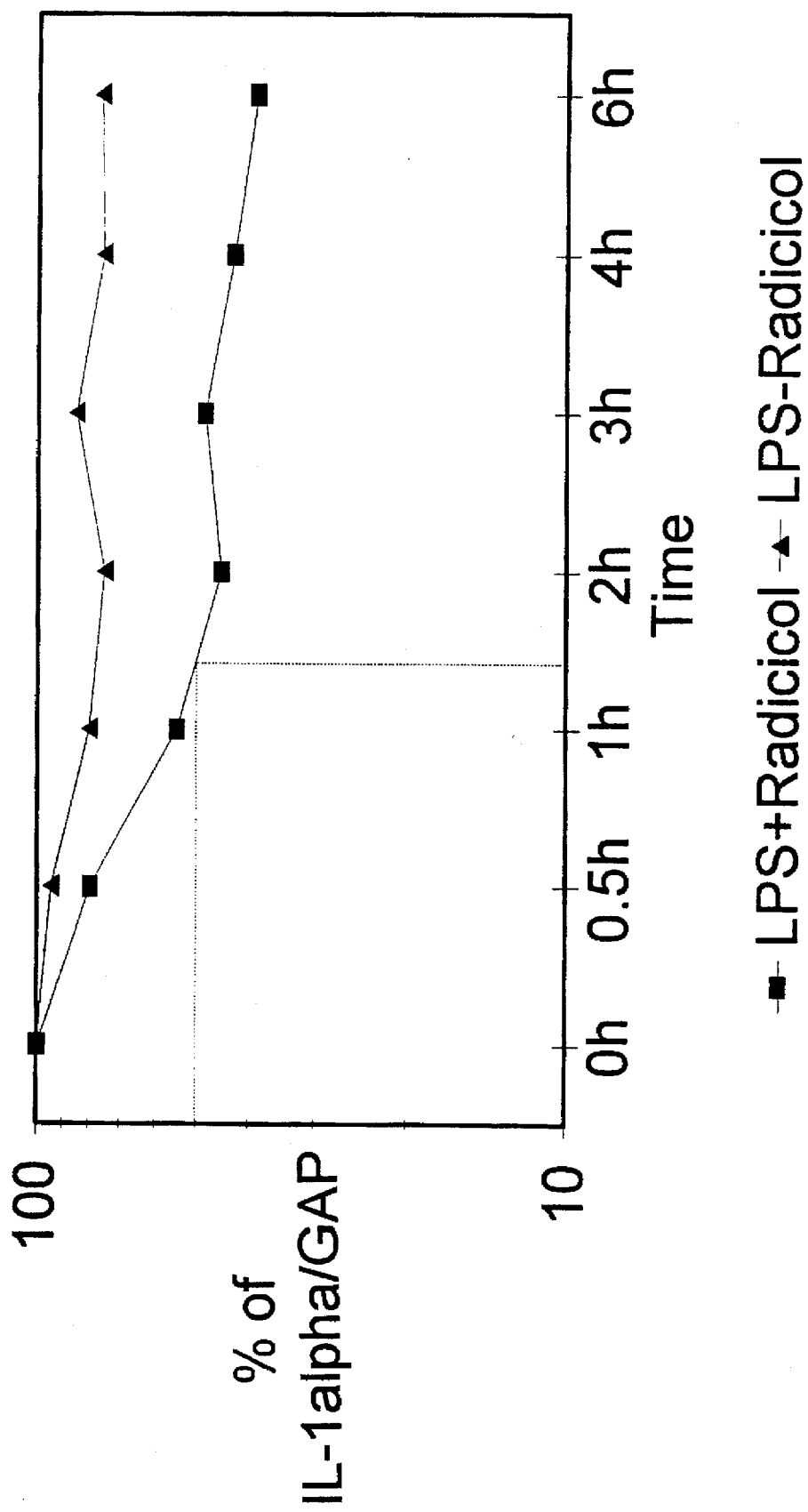
Figure 17D:
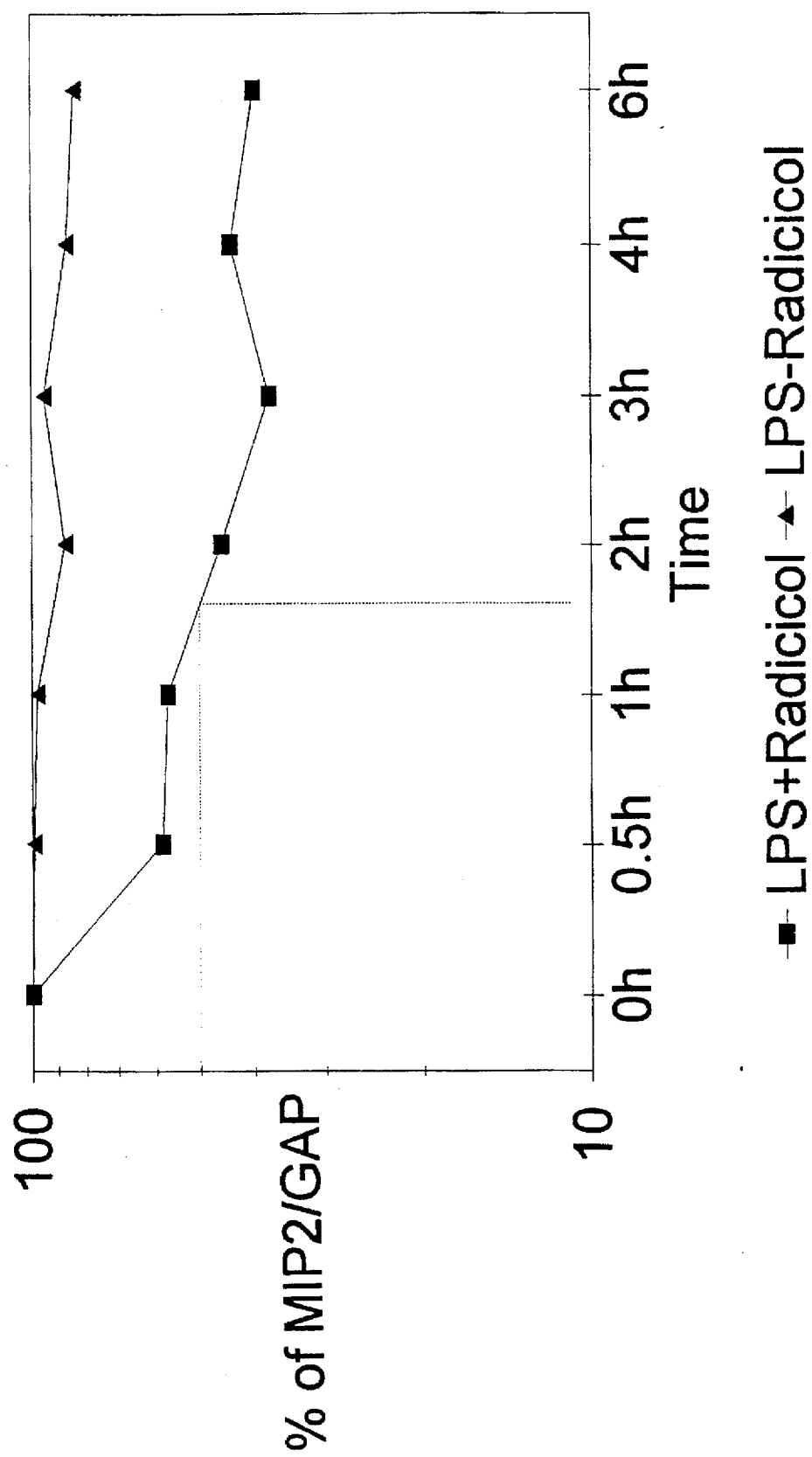
Figure 17E:
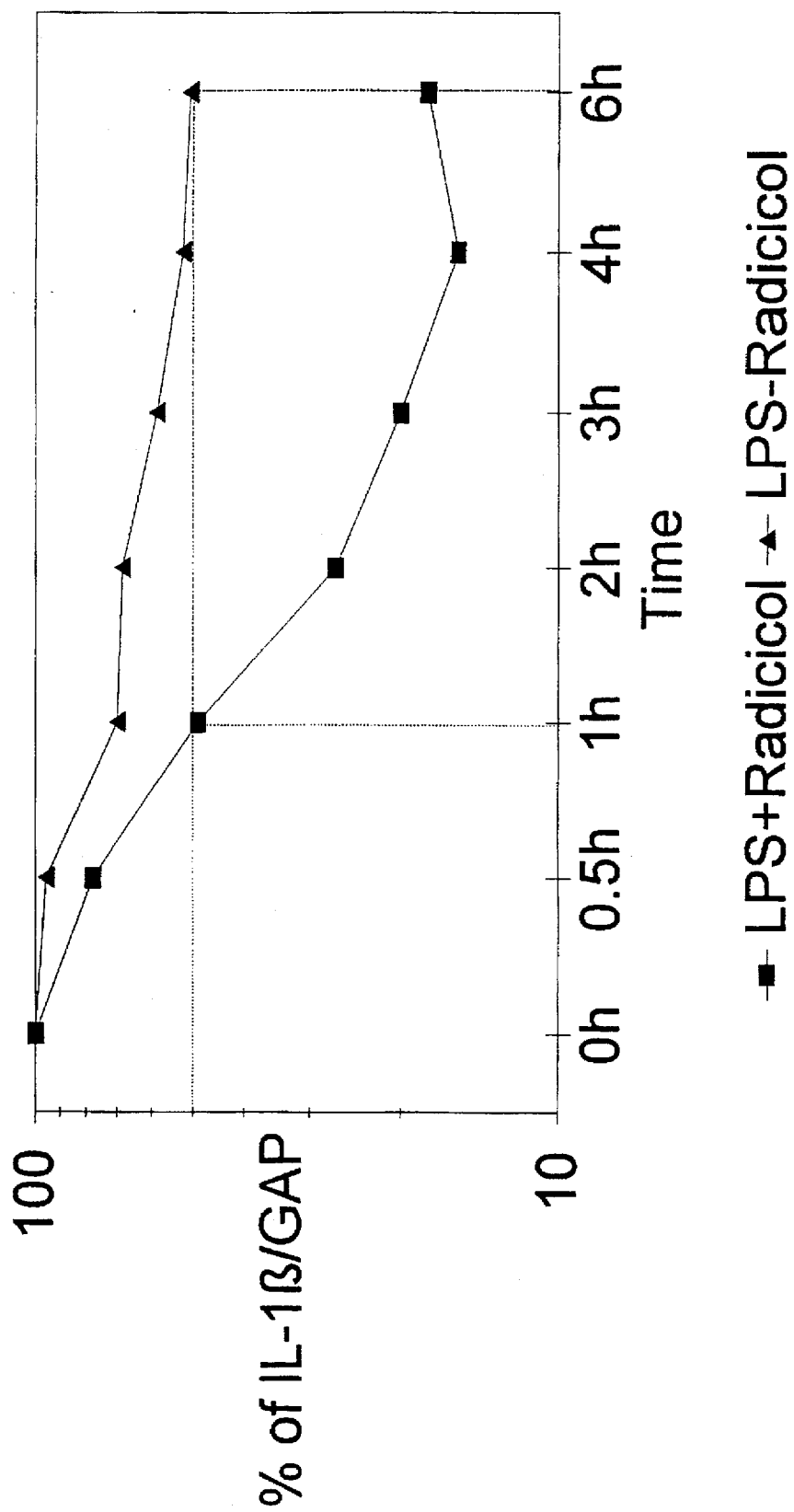
Figure 17F:
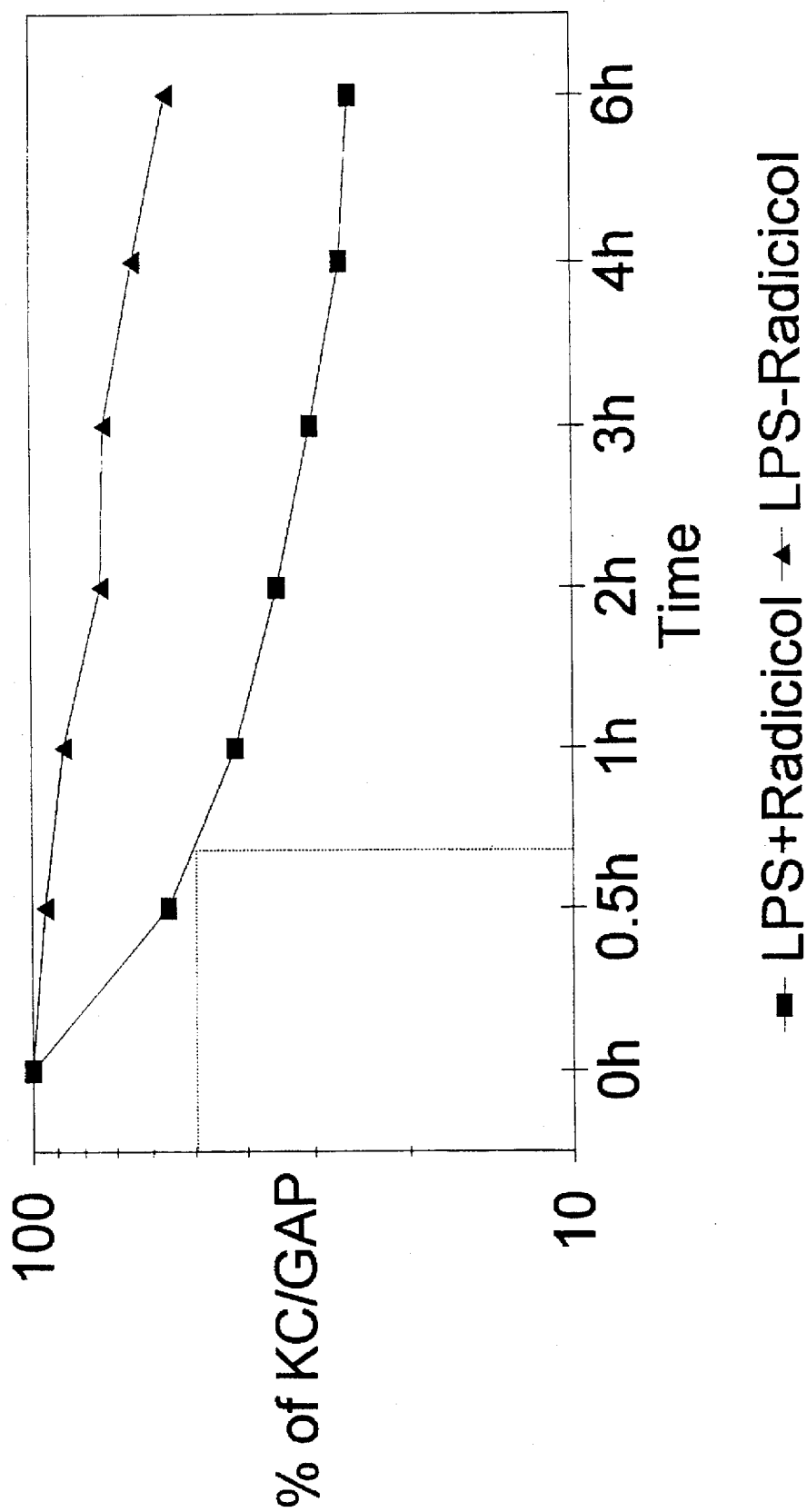
Figure 17G:
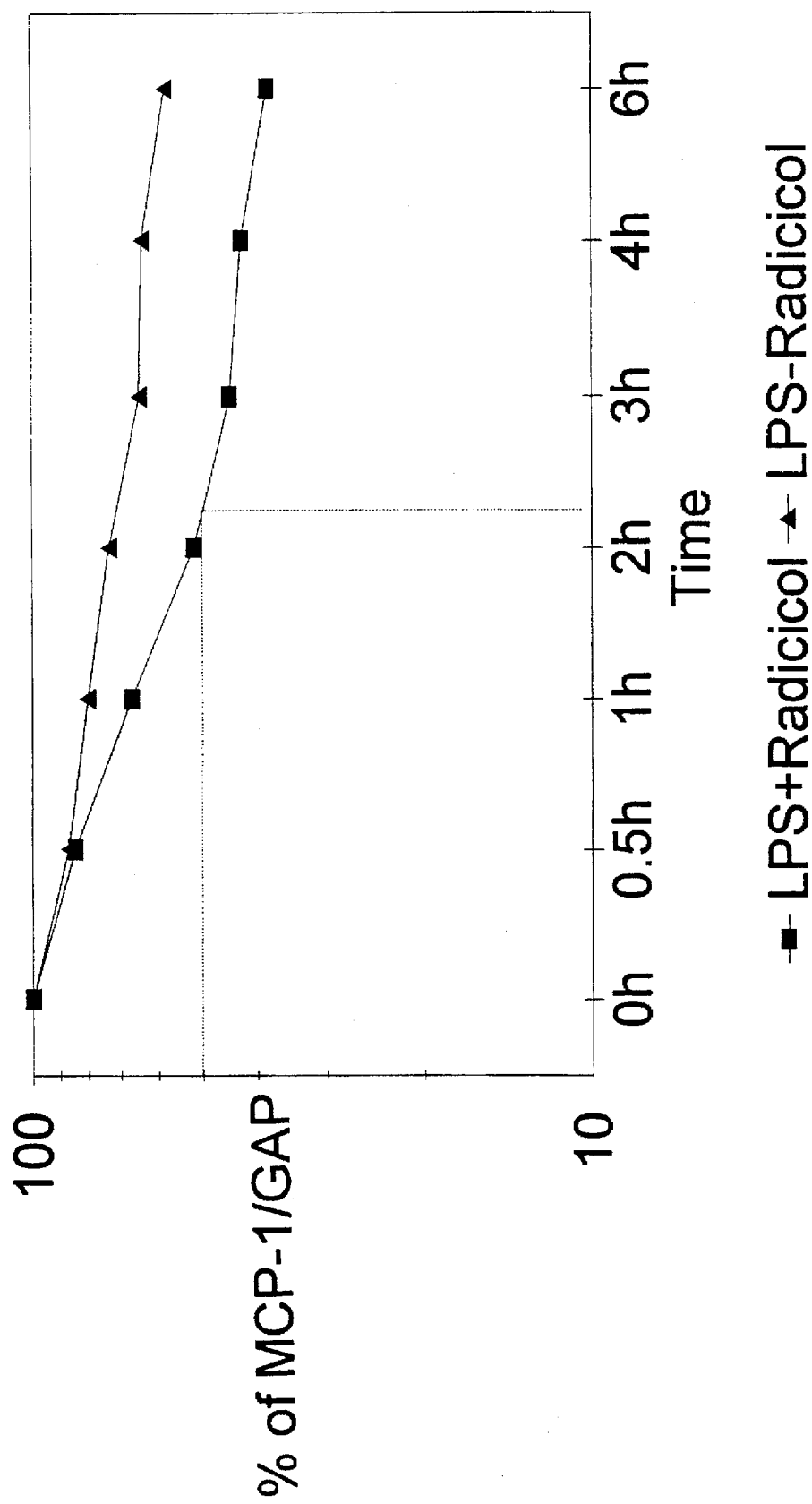
Figure 17H:
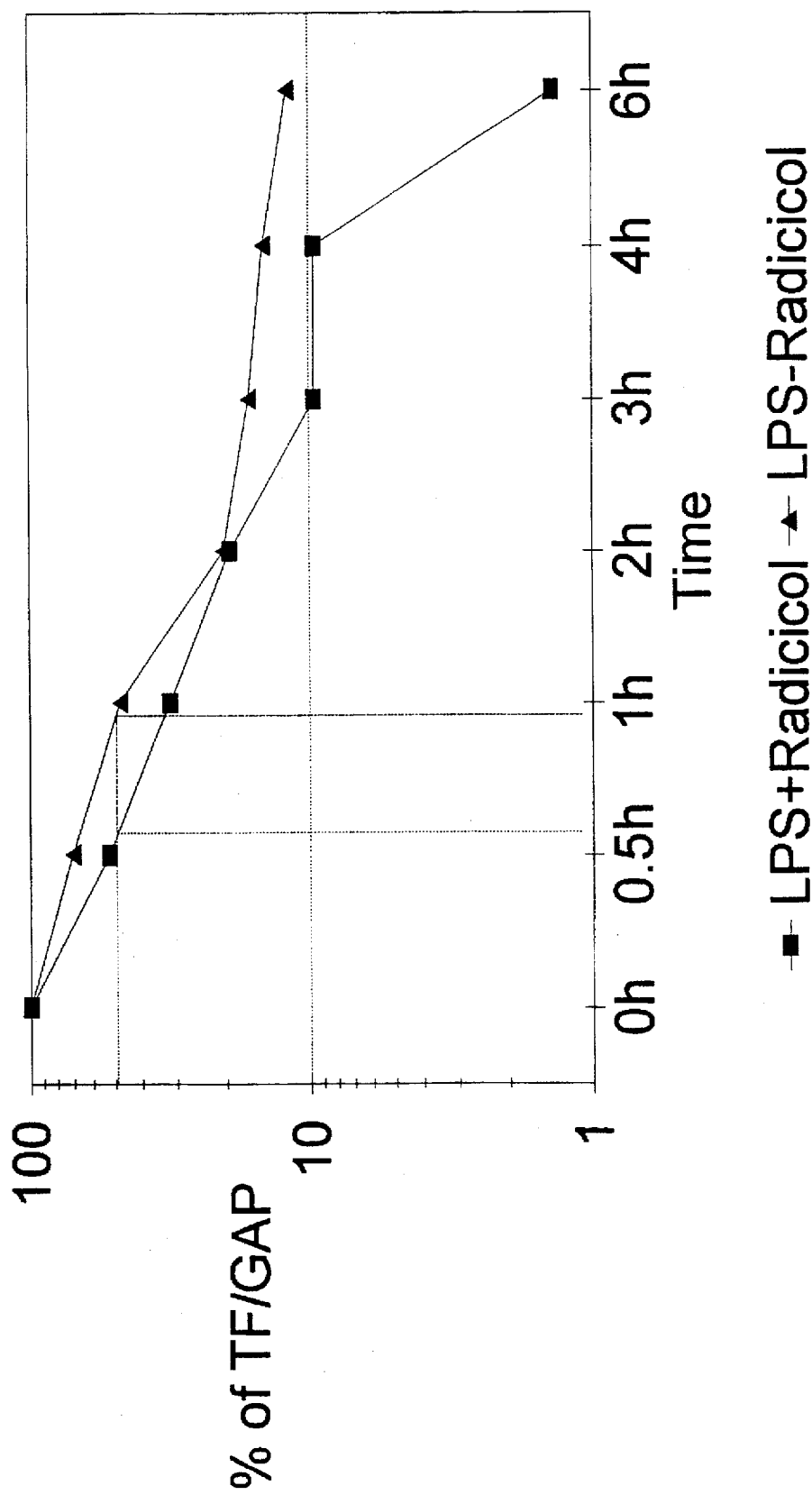
Figure 17I:
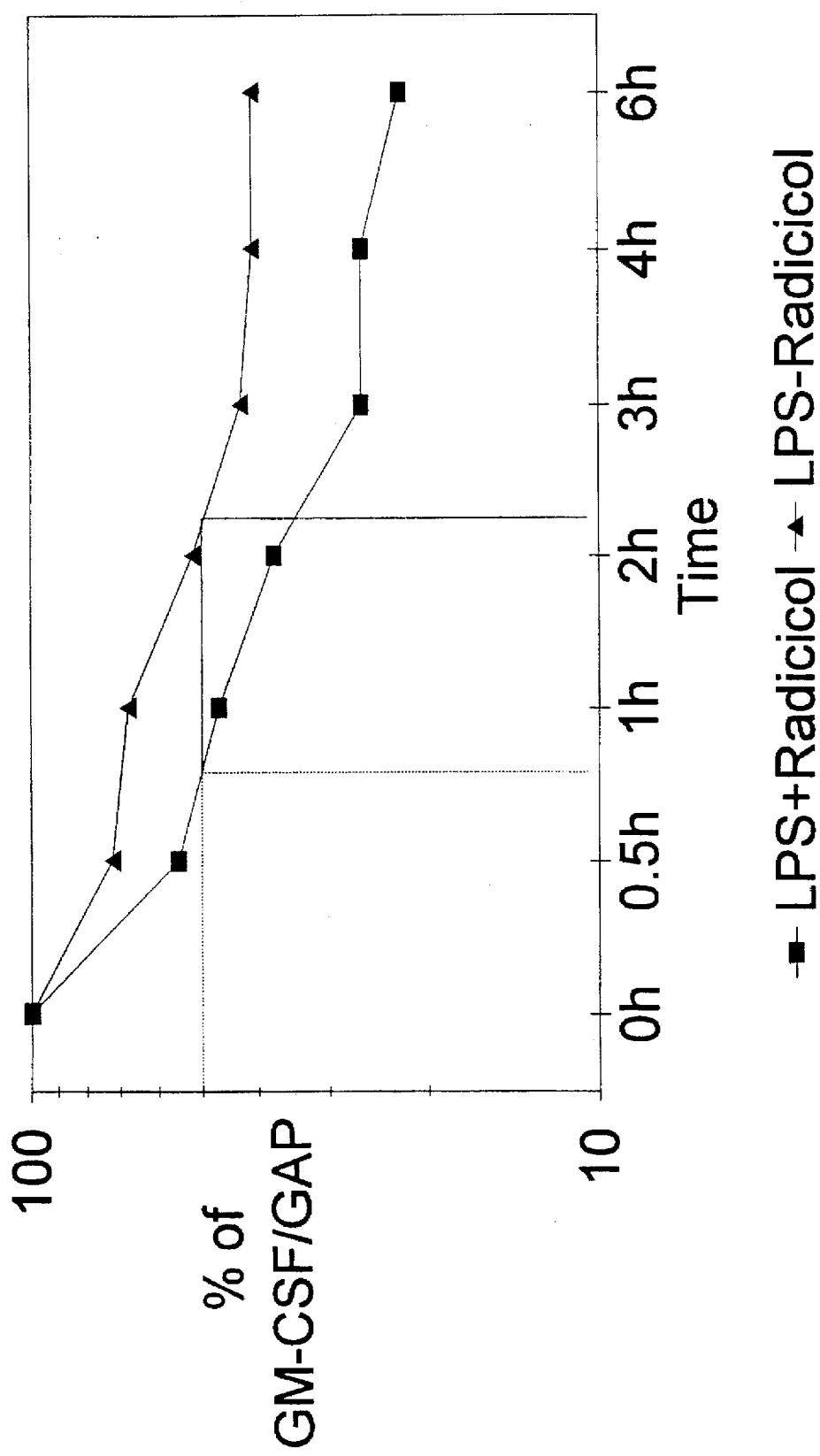
Figure 17J:
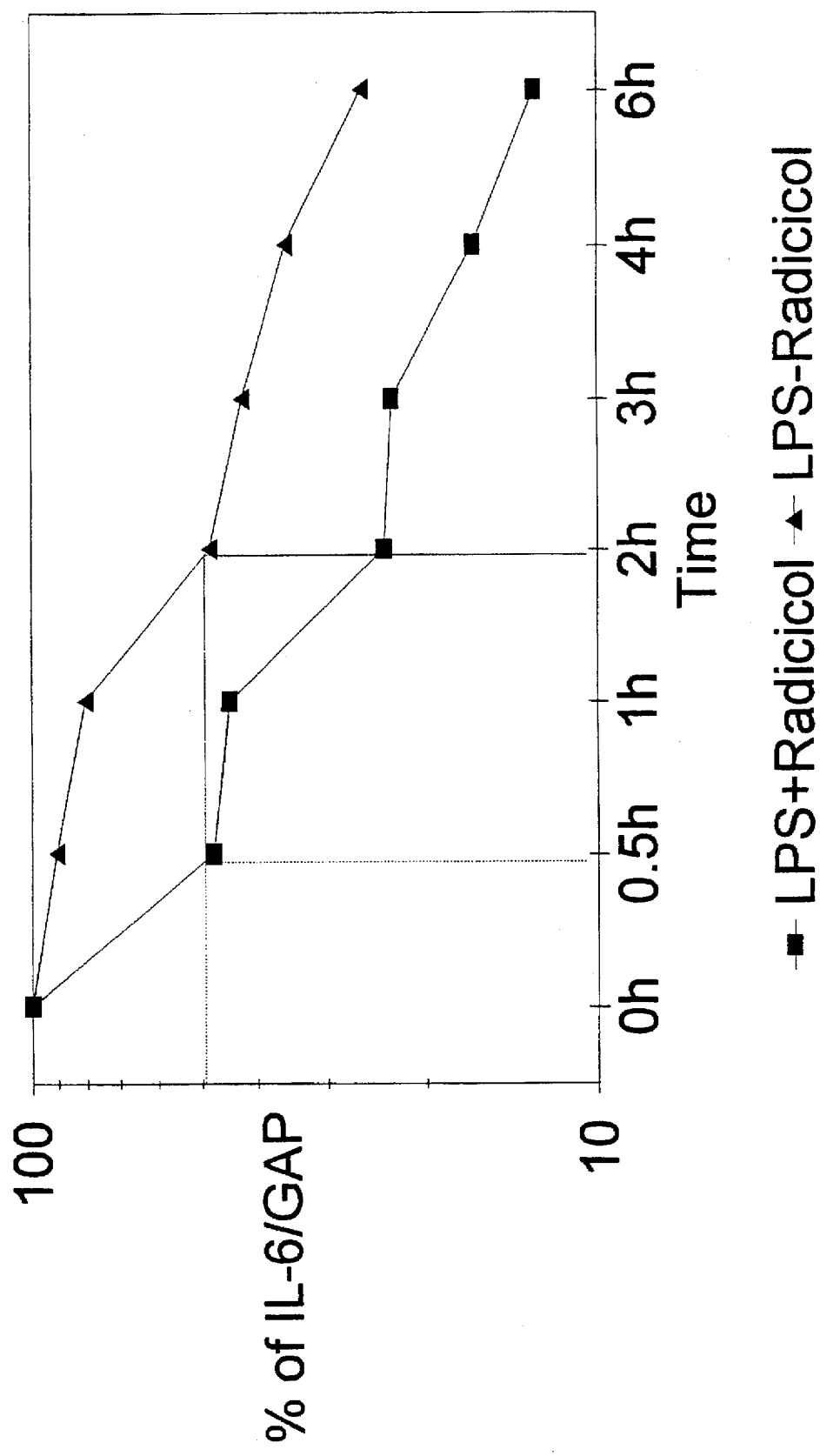
Figure 17K:
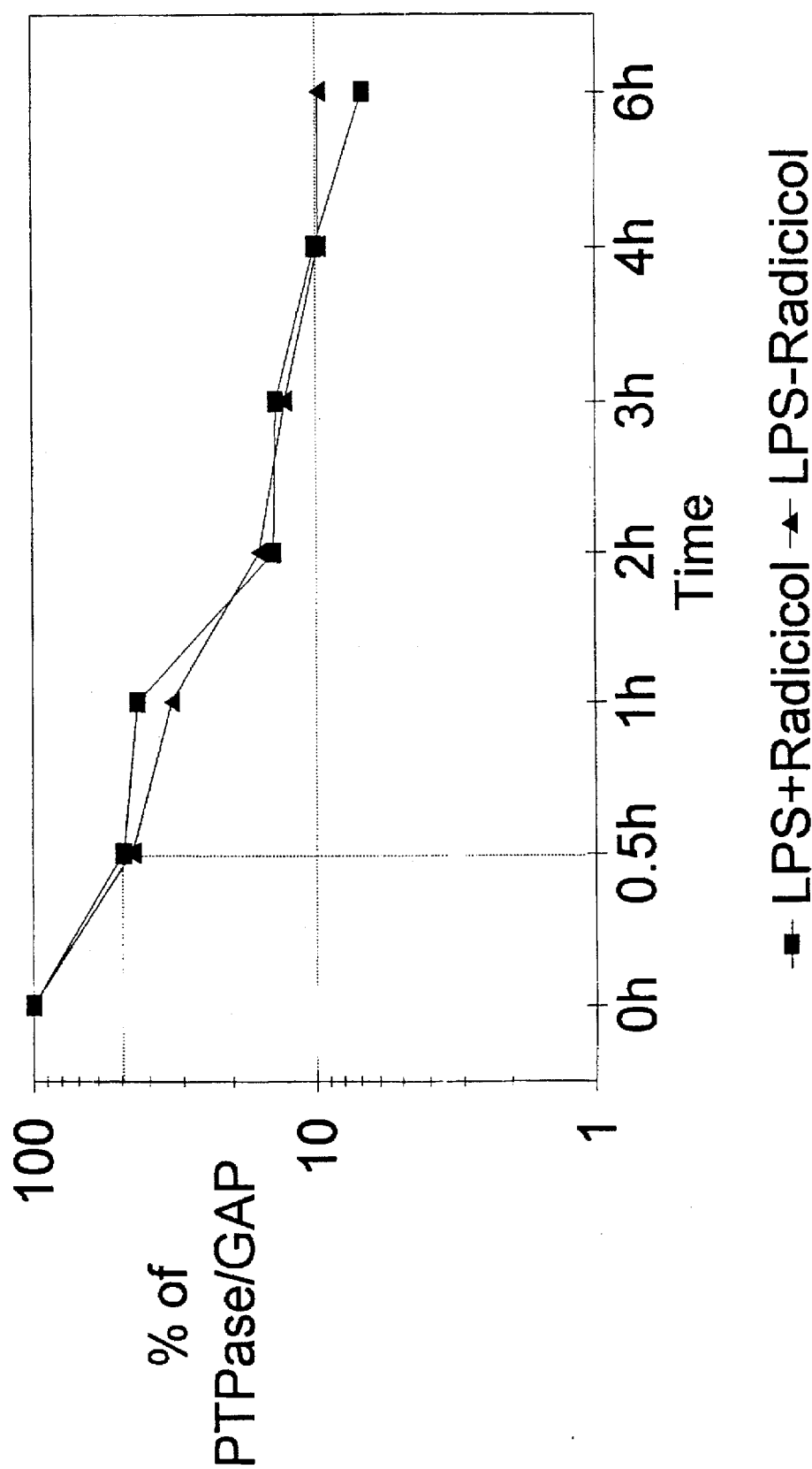

FIG. 18 shows in vivo effects of radicicol on expression of COX-1, COX-2 and glyceraldehyde-3-phosphate dehydrogenase in rats with experimental glomerulonephritis. Glomerular injury was induced in rats with nephritogenic doses of anti-glomerular basement membrane (GBM) antibodies, as described in Example 1. Radicicol or vehicle was infused through the renal artery for 60 minutes at the dose of 10 µg/100 g body weight per minute. The rats were sacrificed after 4 hours and 24 hours following anti-GBM antibody injection. The total RNA extracted from whole kidneys and glomeruli was used for RNase protection assay to determine levels of COX-1, COX-2 and GAP mRNA.

Levels of COX-2 mRNA, but not COX-1 mRNA, were dramatically decreased in glomeruli of rats (n=3) treated with radicicol as compared to the vehicle-treated group (n=3), as shown in FIG. 18. This change in COX-2 mRNA levels was correlated with the reduction of $PGE_2$ levels in glomeruli of rats treated with radicicol (Table 2). Levels of $PGE_2$ in the whole kidney were not affected by radicicol treatment, suggesting that this reduction is caused by the inhibition of the expression of inducible COX-2 but not that of COX-1.

TABLE 2

EFFECTS OF RADICICOL TREATMENT ON PGE2 LEVELS IN KIDNEY AND GLOMERULI OF RATS WITH EXPERIMENTAL GLOMERULONEPHRITIS

|  | KIDNEY Vehicle | (ng/mg protein) Radicicol | GLOMERULI Vehicle | (ng/mg protein) Radicicol |
|---|---|---|---|---|
| 4 hours | 1110 ± 29 | 1114 ± 140 | 3722 ± 536 | 2486 ± 150 (p ≦0.05) |
| 24 hours | 1185 ± 68 | 1097 ± 109 | 2506 ± 32 | 1170 ± 19 (p ≦0.001) |

Radicicol (10 µg/100 g body weight/minute) was infused through renal artery for 60 minutes. Rats were sacrificed after 4 hours and 24 hours following anti-glomerular basement membrane antibody injection. Levels of $PGE_2$ were determined by radioimmunoassay after Sep-Pak purification of ethanolic extract of tissue samples. Values are the mean ± SEM of 3 samples.

SUMMARY

In summary, Src family tyrosine kinases were the major tyrosine phosphorylated proteins in LPS-stimulated macrophages. Radicicol suppressed tyrosine phosphorylation of these kinases. Radicicol suppressed the expression of COX-2, but not COX-1, as well as IL-1 and TNF-α in LPS-stimulated macrophages, and in glomeruli of rats with experimentally induced glomerulonephritis in which COX-2 expression is known to be enhanced. Thus, radicicol is a potent inhibitor for the expression of COX-2 both in vitro and in vivo. Other protein tyrosine kinases inhibited the COX-2 expression in LPS-stimulated macrophages. These results suggest that the inhibition of COX-2 expression by radicicol is at least in part mediated through the inhibition of protein-tyrosine kinases in LPS-stimulated macrophages. The magnitude of the inhibition of COX-2 protein synthesis by radicicol was much greater than that of the steady state levels of COX-2 mRNA. The rate of COX-2 mRNA degradation was not significantly affected by radicicol. Taken together, these results suggest that the inhibition of COX-2 expression by radicicol occurs mainly at post-transcriptional steps. In addition, the results of the RNase protection assays indicate that radicicol also inhibits the expression of several pro-inflammatory cytokines, including IL-1 and TNF-α.

Although the invention has been described with reference to the presently preferred embodiments, it should be understood that various modifications can be made without departing from the spirit of the invention. Accordingly, the invention is limited only by the following claims.

We claim:

1. A method of treating an immunopathological disorder having an etiology associated with production of a proinflammatory agent, wherein the agent is selected from the group consisting of interleukin- 1 (IL-1), interleukin-6 (IL-6), interferon-γ (IFN-γ), tumor necrosis factor-α (TNF-α), granulocyte macrophage-colony stimulating factor (GM-CSF), the growth related gene KC, cyclooxygenase-1 (COX-1), cyclooxygenase-2 (COX-2), macrophage chemotactic protein (MCP), inducible nitric oxide synthetase (iNOS), macrophage inflammatory protein (MIP), tissue factor (TF), phosphotyrosine phosphatase (PTPase), and endotoxin, the method comprising administering to a subject with the disorder, a therapeutically effective amount of a compound of the formula:

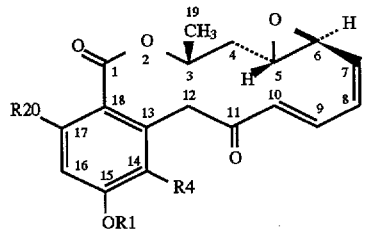

where R1 and R2 are independently H or —COR3; R3 is H, 1–50C alkyl, 1–20C alkoxy, 2–30C alkenyl, 2–30C alkenyloxy, 2–10 alkynyl, 6–14C aryl or aryloxy, a 5–6 membered heterocycle (containing 1–3 N, O and/or S heteroatoms and optionally fused to an aryl group), 3–8C cycloalkyl (optionally fused to aryl) or 5–8C cycloalkenyl; and R4 is a halogen.

2. The method of claim 1, wherein the immunopathological disorder is septic shock.

3. The method of claim 1, further comprising administering an antibiotic to the subject.

4. The method of claim 1, wherein the immunopathological disorder is selected from the group consisting of microbial infection, malignancy and metastasis, asthma, coronary restenosis, autoimmune diseases, cirrhosis, endotoxemia and reperfusion injury.

5. The method of claim 1, wherein the administering of radicicol is at a dosage from about 10 µg/kg to 1000 µg/kg.

6. The method of claim 1, wherein the administering of radicicol is at a dosage from about 10 µg/kg to 500 µg/kg.

7. The method of claim 1, wherein the administering of radicicol is at a dosage from about 10 µg/kg to 200 µg/kg.

8. The method of claim 1, wherein the administering of radicicol is selected from the group consisting of subcutaneous, intravenous, and transdermal.

* * * * *